United States Patent [19]

Falkow et al.

[11] Patent Number: 5,662,908
[45] Date of Patent: Sep. 2, 1997

[54] INVASIVE MICROORGANISMS

[75] Inventors: Stanley Falkow, Portola Valley, Calif.; Ralph Isberg, Brookline, Mass.; Virginia Miller, Van Nuys; Joseph W. St. Geme, III, Redwood City, both of Calif.; Catherine A. Lee, Newton, Mass.

[73] Assignee: The Board of Trustees of the Leland Stanford Jr. University, Palo Alto, Calif.

[21] Appl. No.: 216,086

[22] Filed: Mar. 21, 1994

Related U.S. Application Data

[63] Continuation of Ser. No. 844,470, Mar. 2, 1992, abandoned, which is a continuation-in-part of Ser. No. 644,826, Jan. 23, 1991, Pat. No. 5,239,066, which is a continuation-in-part of Ser. No. 559,904, Jul. 30, 1990, abandoned, which is a continuation-in-part of Ser. No. 340,375, Apr. 19, 1989, Pat. No. 5,310,654, which is a continuation-in-part of Ser. No. 761,222, Jul. 31, 1985, abandoned.

[51] Int. Cl.$^6$ .................. A61K 39/112; A61K 39/116; C12N 1/20; C12N 1/21
[52] U.S. Cl. .................. 424/200.1; 435/252.8; 435/252.3; 424/235.1; 424/258.1
[58] Field of Search .................. 435/172.1, 172.3, 435/252.3, 252.8, 879; 424/92, 93 A, 200.1, 235.1, 258.1

[56] References Cited

FOREIGN PATENT DOCUMENTS

91/15572  10/1991  WIPO .................. C12N 1/20

OTHER PUBLICATIONS

Wilson, D.R. et al. 1990 Res. Microbiol. vol. 141 pp. 827–830.

Galan, J.E. et al. 1989 Proc. Natl. Acad. Sci. USA vol. 86 pp. 6383–6387.

Miller, I. et al. 1989, Infect. Immun. vol. 57, pp. 2758–2763.

Elsinghorst, E.A. 1989, Proc. Natl. Acad. Sci. USA vol. 86 pp. 5173–5177.

Hormache, C. 1991, J. Immunol. Meth. vol. 142 pp. 113–120.

Galan, J.E. et al. 1991, Infect. Immun. vol. 59, pp. 2901–2908.

*Primary Examiner*—Mary E. Mosher
*Attorney, Agent, or Firm*—Flehr, Hohbach, Test, Albritton & Herbert; Richard F. Trecartin; Robin M. Silva

[57] ABSTRACT

Novel methods and microorganisms are provided, where novel genetic mammalian cell invasive capability is imparted to a microorganism by the introduction of an exogenous ail or hil gene. The resulting organisms are then capable of binding to mammalian cells and are transferred to the cytoplasm. Other novel genetic capabilities may be imparted to the unicellular microorganism, which may serve as a vaccine for one or more pathogens or may introduce genetic capabilities or foreign molecules into a mammalian host cell. The sequences may be used for an in vitro screen for pathogenicity. Mutant microorganisms having an attenuated invasive phenotype are also disclosed wherein one or more invasive genes have been modified.

9 Claims, 1 Drawing Sheet

INVASIVE MICROORGANISMS

CROSS-REFERENCE TO RELATED APPLICATIONS

This is a continuation of application Ser. No. 07/844,470, filed Mar. 2, 1992, now abandoned, which is a continuation-in-part of application Ser. No. 07/644,826, filed Jan. 23, 1991, now U.S. Pat. No. 5,239,066, which is a continuation-in-part of application Ser. No. 07/559,904, filed Jul. 30, 1990, abandoned, which is a continuation-in-part of application Ser. No. 07/340,375, filed Apr. 19, 1989, now U.S. Pat. No. 5,310,654, which is a continuation-in-part of application Ser. No. 06/761,222, filed Jul. 31, 1985, abandoned, each of which are incorporated herein by reference.

The development of this invention is funded at least in part by the Department of Defense under contract DAMD 17-82-C-2002 and by the NSF under NSF grant PCM 83-06654 and the Government may have rights in this invention. The development of the invention was also funded in part by the Jane Coffin Childs Memorial Fund.

INTRODUCTION

1. Technical Field

The field of this invention concerns compositions related to invasive capability of microorganisms.

2. Background

For many species of microorganisms, invasion and survival within mammalian cells is central to establishing a successful host-parasite relationship. This localization within host cells may protect the microorganism to cross epithelial barriers and subsequently become systemically distributed. The precise mechanisms by which bacteria enter host tissues have been unclear. The invasive character of pathogens, while deleterious to the health and viability of host cells, does provide a mechanism for transfer of molecules and aggregates across an intact cellular membrane. Thus, if the invasive quality could be transferred to an innocuous microorganism strain, such a strain could serve as a vehicle for transporting molecules of interest into the cytoplasm and organelles of host cells.

There is a further consideration in that the microorganism could provide for the transfer of genetic material into the mammalian host cell. In this manner, novel genetic capabilities could be imparted to the host cell. One capability of interest is the synthesis of surface membrane proteins or envelope proteins of pathogens. These proteins can then serve as antigens to provide a strong immune response, without the host having to suffer the effects of infection by the pathogen.

RELEVANT LITERATURE

The invasion of epithelial cells by *Yersinia pseudotuberculosis* is reported by Bovallius and Nilson, (1975) *Can. J. Microbiol.* 21:1997–2007 and Bolin et al., (1982) *Infect. Immun.* 37:506–512. The factors associated with *Shigellae* invasiveness are described by Hale et al., (1983) *Infect. Immun.* 40:340–350. Sansonetti et al., (1983) ibid 39:1392–1402 and Maurelli et al., (1985) ibid 49:164–171 describe the manipulation of the plasmid in *Shigellae* encoding functions essential for invasiveness.

Isberg and Falkow, (1985) *Nature* 317:262–264 and Isberg et al., (1987) *Cell* 50:769–778 describe the invasion locus of *Yersinia pseudotuberculosis*. Falkow et al., Reviews of Infectious Diseases, 9 Supp. 5 S450–S455 (1987) describes the *Yersinia* gene inv. Miller and Falkow, (1988) *Inf. and Imm.* 56:1242–1248 describe a second invasion gene named ail (for attachment invasion locus). Miller et al., (1989) *Science* 243:916–922 describe factors involved with virulence of bacterial pathogens. Finlay et al., *Science* 243:940–943 describe invasion gene of *Salmonella*.

The nucleotide sequence of the *Y. enterocolitica* ail gene is described in Miller et al., (1990) *Bacteriology* 172:1062–1069. See also Miller et al., (1989) *Infect. and Immun.* 57:121–131. St. Geme, J. W. et al. (1990) *Infect. and Immun.* 58, 4036–4044 describe the adherence and invasion of *Heamoplilus influenzae* into human epithelial cells. For a review of bacterial invasive strategies, see Finlay and Falkow (1989)*Microbiological Reviews* 53:210–230.

SUMMARY OF THE INVENTION

Methods and compositions are provided for introducing macromolecules into mammalian host cells using substantially non-pathogenic microorganisms to which have been imparted novel invasive capability. The genetic capability of invasiveness is transferred from an invasive microorganism to a recepient host, whereby the recipient may now invade mammalian cells and be used as a carrier for various molecules. In this manner, molecules which cannot normally cross the cell membrane may be transported across the membrane while retaining an intact membrane and a viable host cell. In one application, the modified unicellular microorganism may be used as a vaccine by providing genetic capability for expressing surface membrane proteins or envelope proteins of various pathogens. Protocols are also provided for screening invasive pathogens for the genetic sequences associated with such capabilities and transferring such genetic capabilities to non-pathogenic (innocuous) hosts. The invention also provides mutant microorganisms wherein one or more invasive-type genes are modified to attenuate the invasise phenotype of the microorganism.

DESCRIPTION OF THE SPECIFIC EMBODIMENTS

Figure 1A:
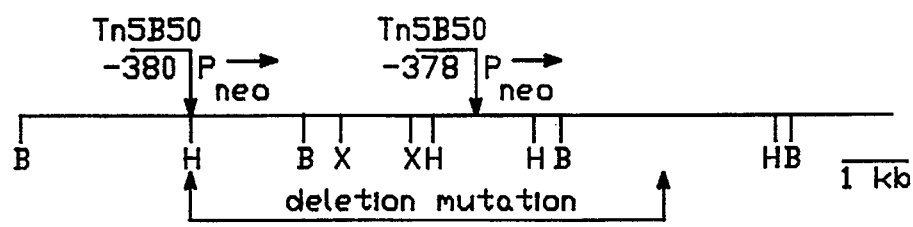
FIG. 1A depicts the restriction map of 20 kb of *S. typhimurium* chromosomal DNA encompassing the hil locus. B, BamH1; H, HindIII; X, XhoI. The position and orientation of Tn5B50 insertions are shown above the chromosomal map. The limits of deletion mutation are shown below the chromosomal map. Presumably, placement of Tn5-428 between the rightmost BamHI sites occured prior to deletion between 1550 elements of Tn5B50-380 and the Tn5.

The subject invention provides means for introducing exogenous molecules into mammalian cell hosts employing unicellular microorganisms as the vehicle. The method involves isolating the genetic capability of invasiveness from an invasive unicellular microorganism and transferring the genetic capability to a recipient unicellular microorganism which does not naturally have the transferred gene imparting invasive capability, making any additional modifications in the modified recipient microorganism, as appropriate, and contacting mammalian cells susceptible to invasion by the modified recipient microorganism with the modified unicellular microorganism. Screening protocols are provided for identifying the genetic region associated with invasiveness, which region may be introduced directly into the recipient microorganism or may be further modified prior to introduction. The recipient microorganism may be used as a vehicle for introducing various molecules, particularly macromolecules, into a mammalian host susceptible to invasion.

The first aspect of the subject invention to be considered are the selection protocols for identifying the genetic capability of invasiveness. In a first embodiement of the selection protocols, an invasive unicellular microorganism is selected, the genome fragmented, either mechanically or by partial or complete digestion with one or more restriction enzymes, and the fragments joined to an appropriate replication system for introduction into a non-invasive unicellular microorganism. The replication system may be derived from a plasmid or a virus, desirably providing for a vector having a copy number equal to or greater than one and the copy number may be 200 or greater.

The vector should neither be lethal to the host nor result in an undue reduction in viability. Desirably, the vector should provide a marker which allows for selection of recipient unicellular microorganisms which include the vector. Various markers are available, such as biocide resistance, e.g., antibiotic resistance and heavy metal resistance, genes imparting prototropy to an auxotrophic host, immunity, and the like.

The genomic fragments inserted into the vector will usually be at least about 2 kb and not more than 50 kb, generally ranging from about 5 to 20 kb. Conveniently, a viral vector may be employed which provides for selection of fragments in the desired range based on the packaging requirements. While it is not essential to select for the microorganisms which have received the vector, it is preferable to select for recipient unicellular microorganisms. Desirably, the vectors should be capable of stable episomal maintenance or integration into the genome. Where integration is involved, amplification of the gene is desirable.

The genome of invasive unicellular microorganisms are mechanically sheared or digested with one or more restriction enzymes, either partially or completely, to provide fragments in the range of about 2 to 20 kbp. The fragments are then inserted into an appropriate vector, such as a viral vector, e.g., cosmid, or plasmid vector, e.g., pBR322. Non-invasive unicellular microorganisms are transfected or transformed with the vectors and modified organisms are selected by means of a marker, e.g., antibiotic resistance. The desired clones are then enriched by the following procedure.

The surviving organisms are cloned, suspended in an appropriate nutrient medium and introduced onto confluent layers of invasive susceptible mammalian cells. The cells are allowed to incubate for a sufficient time, usually at least about 1 hour, and less than about 12 hours, conveniently from about 2 to 6 hours, under conditions which maintain viability of the cells. The monolayer is then stringently but carefully washed under conditions which remove nonadherent recipient microorganisms, so that only adherent microorganisms remain bound to the mammalian cell monolayer. The mammalian cells that have internalized the modified organism are then released from the monolayer by treatment with a mild detergent, e.g., a nonionic detergent, generally at a concentration in the range of about 0.1 to 2%, more conveniently about 0.5 to 1.5%, in an aqueous medium. Any mild technique which allows for the viability and release of the modified microorganism from the mammalian cells may be employed. The released modified microorganisms are then expanded and cloned.

Transposon mapping may be employed for identifying the transposon insertions which destroy invasive capability. In this manner, the structural gene with its associated regulatory signals can be mapped to a particular site on the fragment. Other techniques involve employing partial digestions, cloning and screening for invasive capability, followed by sequencing and identifying specific sequences associated with transcription and translation as indicative of the structural gene and its associated regulatory signals.

In a further embodiment of the protocols to identify genes capable of imparting an invasive phenotype to an otherwise non-invasive organism, an invasive microorganism is selected for analysis. The organism is then exposed to a transposon under conditions which permit its integration into the genome of the selected invasive microorganism. The transposon used is capable of causing constitutive or inducible expression of the genomic DNA at or near the site of integration. Such transposons are well known to those skilled in the art and generally comprise a transposon containing an appropriate promoter at or near one end of the transposon. In addition, the transposon generally contains a selection marker which permits selection of those invasive microorganisms successfully transformed with the transposon.

The mutated invasive microorganisms formed upon integration of the above transposon are then assayed to determine the relative invasiveness of such mutated microorganisms as compared to the wild-type invasive microorganism. Those mutated microorganisms which contain a transposon at or near an invasive-type gene with the promoter of the transposon orientated in the proper direction are capable of expressing the invasive-type gene under appropriate conditions. When an inducible promoter is used, such conditions include those to which the inducible promoter is responsive.

Depending upon the relative strength of expression regulation as between that of the wild-type microorganism and the mutated microorganisms, the transposon mediated expression of an invasive-type gene can confer a phenotype demonstrating greater or lesser invasive capability. In either case, the change in invasive capability as compared to the wild-type invasive microorganism provides an indication that the transposon has integrated at or near an invasive-type gene or at a gene which is an activator of an invasive-type gene. Mutants of the latter type, however, can be readily distinguished by subsequent analysis from those wherein the transposon has integrated at the invasive-type gene.

Once a mutant is selected, the site of integration of the transposon is mapped and the orientation of the promoter of the transposon determined. The DNA downstream from the transposon promoter is sequenced to detect an open reading frame encoding the putative invasive-type protein. If the sequence corresponds to a known non-invasive gene, further analysis is generally not necessary, although further analysis can be conducted to confirm the non-invasive character of the gene. If there is no known sequence correspondance or if further analysis is desired, the thus identified open reading frame DNA either with the transposon promoter, or in conjunction with a different promoter system, is cloned and thereafter used to transform a non-invasive microorganism such as a non-invasive *E. coli*. Those non-invasive microorganisms which acquire an invasive phenotype, e.g., based upon their invasiveness of cultured mammalian cells as described herein, contain DNA of an invasive-type gene from the original invasive-type organism. Those which do not confer an invasive phenotype are presumed to encode an activator of the invasive-type gene.

In a specific embodiment of this protocol, it is preferred that the detection of a change in invasive capability upon transposon integration be based upon an increase in the invasion phenotype of the mutated microorganism as compared to the wild-type microorganism. Accordingly, conditions are chosen for assaying invasiveness which decrease or eliminate the invasiveness of the wild-type organism. Since many invasive microorganisms are invasive under an anaerobic conditions, an invasiveness assay under aerobic conditions often results of down regulation of the invasive phenotype in the wild-type microorganism. Under such conditions, the promoter of the transposon is more likely to up-regulate the invasive-type gene as compared to the wild-type gene assayed under substantially the same conditions.

If desired, an identified gene which is capable of conferring an invasive phenotype to an otherwise non-invasive microorganism can be modified for a particular application. For example, the regulatory signals, particularly the transcription initiation signal, may be modified by the addition or substitution of the native transcriptional initiation region with a transcriptional region associated with a different gene. In this way, one can provide for low or high levels of constitutive or inducible expression of the DNA sequence encoding for invasive capability. Various transcriptional initiation regions or promoters are available, which are temperature sensitive, are inducible in the presence of various metabolites or nutrients, and the like. Therefore, a transcriptional initiation region may be employed which is regulated by the unicellular microorganism host and the invasive capability may be activated or inactivated by physically or chemically changing the environment of the microorganism host. Thus, nutrients and metabolites such as glucose, tryptophan, histidine, galactose, lactose, may be employed to induce or repress the expression of the invasive gene (inv). The inducible transcriptional regulatory region may be selected in accordance with the mammalian host, depending upon whether the coinducer or corepressor is naturally found in the mammalian host or can be administered to the host.

Constructs may then be prepared which may be used for introducing invasive capability into an appropriate unicellular microorganism host. Depending upon the purposes for invasiveness, a wide variety of bacterial or eukaryotic microorganism hosts may be employed. The subject method provides for introduction of DNA capability into a mammalian cell where the unicellular microorganism is employed as the vehicle for introduction of the DNA capability into a mammalian cell. For example, a shuttle vector may be provided in the invasive microorganism host which has the capability for replication in the mammalian cell as well as the unicellular microorganism, where the shuttle vector may exist as an episomal element or become integrated into the mammalian cell genome. In this manner, unicellular hosts for cloning may be used directly for the transfer of DNA into a mammalian cell host with high efficiency. Thus, a wide variety of genetic capabilities can be introduced into mammalian hosts, for example, the expression of lymphokines, hormones, enzymes, surface membrane proteins, and the like, such as interferons, interleukins, growth factors, hydrolases, oxidoreductases, receptors, antibodies, histocompatability antigens, etc.

A second manner in which the invasive organism may be used is as a vaccine. For this purpose, in addition to the invasive genetic capability, genes encoding for surface membrane proteins, capsid proteins, or envelope proteins, singly or in combination, may be introduced into the invasive modified microorganism host for injection into a mammal to induce an immune response. The genes encoding for the antigens may be obtained from a wide variety of pathogens, including viruses, prokaryotes, e.g., bacteria, eukaryotes, e.g., fungi, protists, or the like, or such intermediate species as chlamydia. In many cases, the gene of interest is known and available or may readily be isolated. Where not known, the techniques employed for identifying specific structural genes can be employed for identifying the genes coding for the desired antigen.

A third manner in which the invasive organism may be used is as a vehicle for the introduction of molecules, particularly macromolecules, into a mammalian cellular host, either in vitro or in vivo. For example, cytotoxic resistance provided by an enzyme could be transferred into cells or a cytotoxic agent, e.g., aminoglycosides, hybritoxins, etc., non-cytotoxic to the microorganism, could be introduced into mammalian cells. Dyes or other contrast agents could be introduced into the cells for visualization of cell features. Labelled antibodies could be introduced into the cells to define the location of particular antigens. Invasion proteins may be used to introduce particles, such as colloidal particles, liposomes, slowly degrading or slow release particles, cells, or the like, where the particles may include drugs, dyes, nucleic acid, antibodies, or other substances which may have physiological activity. The invasion proteins may be bound non-diffusibly to the particles, either covalently or non-covalently. The literature has numerous examples of commercially available cross-linking agents for joining proteins to other proteins, sugars, synthetic organic polymers, both addition and condensation, and the like.

Invasion proteins may also be used to bind mammalian cells to a surface. Thus in cell cultures, cells may be reversibly bound to a surface, isolated or otherwise be manipulated. Other uses will also be apparent.

A large number of mammalian replication systems and vectors are available, particularly viral replication systems, such as SV-40, adenovirus, bovine papilloma virus, etc. See, for example, Southern and Berg, *J. Mol. Appl. Genet.* (1982) 1:327–341; and Mulligan and Berg, *Proc. Natl. Acad. Sci. U.S.A.* (1981) 78:2072–2076, which are incorporated herein by reference.

One technique would involve employing antisera from a mammalian host who had suffered, particularly was undergoing infection, by the pathogen of interest. The pathogen in culture could be lysed and immunoprecipitated with the antisera from the mammalian host and electrophoresed. A cDNA or genomic library could be prepared from the pathogen. By at least partially sequencing the immunoprecipitated proteins, amino acid sequences could be identified, which could be translated into probes. The probes could then be used for screening the library and identifying sequences complementary to the probes. Once sequences which hybridize to the probes have been identified, where the regulatory sequences are recognized by a prokaryotic host, the prokaryotic host may be transformed with the sequence and the expression product identified. Where the expression of the structural gene is regulated by sequences which are not recognized by prokaryotic hosts, then some manipulation will be required in identifying the sequence coding for the particular antigen and inserting the sequence into an appropriate expression vector. A large number of expression vections exist and various techniques are available for tailoring the structural gene to remove superfluous DNA sequences, particularly 5' to the structural gene. Techniques such as resection with Ba131, primer repair, and in vitro mutagenesis to introduce a convenient restriction site, have all been used successfully.

Antigens of interest may come from a wide variety of sources, such as bacteria, such as *Bordatella, Salmonella,*

*Neisseria, Pneumococcus, Shigellae, Yersinia, Cholera, Meningococcus, Listeria, Mycobacterium,* etc.; viruses, such as HTLV-I, -II, and -III, FeLV, HSV-1 and -2, Adenovirus, Varicella, Vaccinia, Hepatitis, Influenza, Measles, Rubella, Smallpox, Typhoid, Yellow Fever, etc. fungi, such as *Candida, Microsporum, Tricpohyton, Arthroderma, Cryptococcus, Blastomyces, Histoplasma, Coccidroides, Paracoccidroides, Aspergillus, Phycomycetes, Sporotorax, Epidermophyton,* etc. other pathogenic microorganisms, such as Chlamydia, Giardia, etc.

The organisms may be administered in any convenient form as a vaccine. Normally, physiologically acceptable carriers will be employed, such as deionized water, phosphate buffered saline (PBS), aluminum hydroxide, sugar or the like. Usually, the dosage will be determined empirically; about $10^4$ to $10^{10}$ cells will be administered to a human host, with proportionate administration based on size to other mammalian hosts. Generally, there will be a first administration, followed by one or more administrations at two to six week intervals. The particular amount administered will depend upon a number of factors, such as the viability of the invasive microorganism in the host, the concentration of the antigen on the surface of the pathogen, the number of different antigens which are present, the level of immune response to the particular antigen(s), and the like. Administration may be orally, by injection, intravenously, intraarterially, subcutaneously, intraperitoneally, etc. The manner of administering live vaccines is well established and may be found in such texts as Basic and Clinical Immunology, eds. Stites, Stobo. Fudenberg and Wells. 4th ed. Lange Medical Publications, Los Altos, Calif., 1982.

The gene coding for the invasive genetic capability may come from any convenient source. A significant number of organisms are known to be capable of invasion, such as *Yersinia, Chlamydia, Legionella pneumophila, Listeria monocytogenes, Mycobacterium tuberculosis, Haemophilus influenzae, Mycobacterium leprae, Salmonella typhosa, Salmonella typhimurium, enteropathogenic E. coli* (EPEC strains), *Brucella abortus, Cryptococcus neoformans, Histoplasma capsulation, Candida albicans, Tripanosoma cruze, Toxaplasma gondi, Leishmania donovani,* etc. Thus, the source organisms for invasive genes may be bacterial, fungal or protozoan. Preferred organisms will be those which provide a single gene which results in invasive capability. The affinity for the mammalian host receptor should be at least about 0.1. Of particular interest are *Yersinia, Salmonella,* and *Haemophilus,* which are demonstrated in the Experimental section as paradigmatic of invasive organisms.

Genes derived from *Yersinia* species, particularly *Y. pseudotuberculosis* and *Y. enterocolitica* provide a gene referred to as inv with a phenotype INV, while the latter provides the additional gene ail with a phenotype AIL. *Salmonella typhimurium,* and group A meningococci, are found to have analogs to the inv and/or ail genes. The inv gene is found not to be homologous to ail. While both genes provide for invasiveness, the host range of ail is different from the inv genes. These ail genes are found to be chromosomal, rather than present on plasmids. In addition, *Salmonella typhimurium* provide an invasive gene referred to as hil (for hyper-invasive locus), having a phenotype HIL.

The non-invasive host which is modified to become invasive may be prokaryotic or eukaryotic and will be selected depending upon its ultimate purpose. Where the organism is to be the vehicle for transfer of DNA into mammalian cells in culture, then any convenient organism may be employed, particularly one which may be used for cloning of the DNA to be transferred. Therefore, many of the strains of *E. coli,* e.g., K12, may be employed as the recipient microorganism which is modified to become invasive. Where the modified microorganism host is to be employed as a vaccine, the host will normally be selected so as to be innocuous (non-pathogenic), to be capable of being viable extracellularly for an extended period of time, preferably at least about 3 days in the vaccinated host, and to be subject to ready clearance in the vaccinated host. Desirably, the modified recipient microorganism will be free of pyrogens, toxins, or other disease symptom causing factors. By innocuous is intended that regardless of the dose or route, no disease will be observed with an immunocompetent host. While pathogenic microorganisms may be employed, particularly attenuated pathogenic microorganisms, these are not preferred, since there is a possibility of reversion to pathogenicity. Microorganism hosts which may be used for modification to invasive capability include besides *E. coli,* members of the genus Staphylococci, Pneumococci, Streptococci, e.g., mutants, Neisseria, e.g., catarrhalis, Veillonella, Lactobacilli, Corynebacteria, Clostridia,, Hemophilic bacilli, Bacteroides, Actinomycetes, Spirochetes, Mycoplasma, etc.

The manner in which the genetic capability for invasiveness is introduced into the recipient microorganism may be any of the convenient techniques including transformation, e.g., calcium precipitated DNA, transfection, transduction, conjugation, fusion, etc. Applicable techniques may be found in Maniatis et al., A Laboratory Manual, Cold Spring Harbor Laboratory, Cold Spring Harbor, N.Y., 1982. As already indicated, a marker will normally be present which allows for selection of those microorganisms which have received the invasive genetic capability. The organisms may then be grown in an appropriate nutrient medium and used as appropriate.

The invasive microorganisms may be used to prepare antisera for passive immunization. Thus, γ-globulin could be prepared which has antibodies to a broad spectrum of pathogens and for strains of a particular pathogen. The γ-globulin may be isolated and purified from serum by ammonium sulfate precipitation and fractionation according to known techniques. Administration to a mammalian host will generally be in amounts of 50 to 500 mg/kg of host in any physiologically acceptable carrier. Administration will usually be by injection, e.g., intravenously. The modified recipient microorganism may also be used in assays for detecting the presence of antibodies to the antigens foreign to the modified microorganism or the antigens themselves. They also may find use in competing with the invasive microorganisms so as to be useful for therapy.

In addition, the subject microorganisms may be used for expression of proteins expressed by the inv, ail or hil gene. Particularly, by having high copy number vectors, the modified foreign microorganisms may be harvested, lysed and the inv, ail or hil protein isolated by conventional ways, e.g., affinity chromatography, electrophoreses, chromatography, etc.

Sequences encoding all or a portion of the invasion genes may be used for diagnosing pathogenicity or virulence. Two fragments of interest from the ail locus are 0.9 kbp AvaI-ClaI fragment from the plasmid pVM103 and a 1.2 kb ClaI-AvaI fragment from the same plasmid or fragments thereof of at least about 50 bp, preferably at least about 100 bp or extensions thereof including the entire ail coding region or locus. In conjunction with the ail probes, a probe referred to as Inv-Ent may be employed, which is a 3.6 kb ClaI fragment obtained from pVM101, or 50 bp fragment thereof, preferably at least a 100 bp fragment thereof. The 3.6 kb fragment comprises most of the inv gene from *Y. enterocolitica* in addition to adjacent sequences.

Alternatively, a probe referred to as Inv-PSTB may be employed which is a 2.4 kb ClaI-XhoI fragment obtained from pRI203. Isberg et al., *Cell* 50:769–778 (1987). Of particular interest is the use of ail specific sequences for detecting pathogenicity. In pathogenic strains multiple copies of sequences having homology to AIL-B are frequently observed. With the Inv probes, a size pattern is observed when the microorganisms DNA is cleaved with EcoRV. These strains may be divided into types I, II, I/II, III, IV and V by the size of fragments observed. This restriction enzyme cuts once within the Inv-Ent probe, but does not cut within the AIL-B or C probes. The various types are defined in the Experimental section where, types I and I/II were found to be pathogenic, while the remaining types were non-pathogenic, with a strong correlation.

To enhance the invasive phenotype, bacteria are grown in an atmosphere of about 1% oxygen by maintaining a gaseous source of oxygen at that level. This may be contrasted with young cultures of laboratory grown cells (which are typically in the mid-log phase of growth) or overnight cultures (which are typically in the stationary phase of growth). By growing cells in 1% oxygen the invasive phenotype is encouraged and the resulting cells may be more readily screened for the presence of the mRNA encoding for invasiveness, for use as vaccines or for studying the mechanism of the regulation of the invasive phenotype.

In addition to the foregoing, one or more structural invasive genes in an invasive microorganisms can be modifidied to attenuate the invasiveness of the microorganism. Such modification is preferably of a structural invasive gene such as inv, ail or hil, each of which encode an invasive protein which, as discussed above, is capable of imparting an invasive phenotype when transferred into an otherwise non-invasive organism. Such modifications include the substitution, insertion or deletion of one or more nucleotides of the invasive gene, preferably within the protein encoding region, although modification within an expression regulation sequence of the selected gene is also contemplated. The techniques for such modifications are well known to those skilled in the art and involve routine manipulations once a gene is identified and selected for modification.

Examples of nucleotide substitution include modification of one or more codons to a premature translation termination signal, substitution of nucleotides within the ribosome binding site, the promoter sequences etc. Examples of nucleotide insertion include transposon insertion into the protein encoding region or regulatory regions required for transcription or translation. While the foregoing are capable of attenuating the invasiveness of a particular microorganism, they are not preferred when the mutated microoorganism is to be used as a vaccine. This is because of the relatively high potential for reversion to the wild type invasive phenotype. Accordingly, when used as a vaccine, the preferred modification of the invasive gene is deletion of nucleotides, preferably deletion of most, and most preferably all of the gene, including the protein encoding and expression regulation sequences.

Microorganisms having attenuated invasiveness are particularly useful as vaccines, either to generate an immune response to the attenuated microorganism or to the protein encoded by exogenous DNA contained within the organism. For example, *Salmonnella typhimurium* is an invasive microorganism which as described herein contains a hyper-invasive gene called hil in addition to the invasive inv gene. The invasive character of the wild-type microorganism often results in systemic infection including septicemia. As a consequence, this microorganism has not been widely used as a live vaccine. However, an attenuated *Salmonella typhimurium*, wherein the hil gene has been inactivated by mutation, such as by deletion of the gene as described in the Examples herein, is expected to have an attenuated invasive phenotype wherein any invasiveness of the microorganism will be mediated by the inv or other invasive gene rather than the hil gene. Since the hil gene is believed to be responsible for the hyper-invasiveness of the organism, hil mutants are expected to be far less invasive than the wild-type organism. Such mutant *Salmonella* therefore should exhibit sufficient invasiveness to bring about a localized low grade infection, e.g. localized to the Peyers patch, sufficient to cause an effective immune response to the mutant *Salmonella*, but insufficient invasiveness to cause systemic infection.

In addition to the foregoing use as a live attenuated vaccine, such hil mutated *Salmonella* can also be used as a vaccine to confer protection against other pathogens. When so used, exogenous DNA encoding an immunogen such as one or more surface membrane proteins, capsid proteins or envelope proteins from a selected pathogen e.g. virus, prokaryote or eukarote, is incorporated into the mutant *Salmonella* in a DNA construct which facilitates expression of the encoding DNA. Such constructs optionally encode a form of the immunogen that contains a functional secretory signal, transmembrane region and anchor region such that the immunogen is presented on the surface of the mutant *Salmonella* to facilitate an immunogenic response.

The following examples are offered by way of illustration and not by way of limitation.

EXAMPLE 1

Enrichment for Invasive Phenotype

A cosmid bank was constructed (Hohn, *Methods in Enzymology* (1979) 68:229–309; Koomey et al., *Proc. Natl. Acad. Sci. U.S.A.* (1982) 79:7881–7885) by ligating a size-fractionated Sau3AI digest of chromosomal DNA isolated from *Y. pseudotuberculosis* strain YPIII ($p^{-}$) (Bolin and Wolf-Watz, *Infect. Immun.* (1984) 43:72–78) into the BamHI site of pREG153 (available from Dr. R. Gill) a cosmid cloning vehicle that encodes resistance to ampicillin and is further characterized by its low copy number (5–8). Aliquots of the ligation mixture were packaged in vitro (Enquist and Sternberg, *Methods in Enzymology* (1979) 68:281–298) into phage lambda heads with an extract prepared from MMSA345 (available from Dr. F. Stahl) and then infected into *E. coli* K12 strain HB101 (Maniatis et al., A Laboratory Manual), selecting for ampicillin-resistant transductants. Pooled bacteria were grown overnight in culture, washed twice in sterile PBS and resuspended to a density of $5\times10^{8}$ bacteria $ml^{-1}$. The washed bacteria (2 ml) were then introduced onto a confluent monolayer containing $1\times10^{7}$ HEp-2 cells grown in RPMI1640 medium (Irvine Biologicals), and incubated for 3 hours at 36° C. in a 5% $CO_2$ atmosphere. Monolayers were then washed 10 times with sterile PBS to remove non-adherent bacteria. Bacterial clones remaining associated with the monolayer were released with 1% Triton X-100 in deionized water, and plated for individual colonies on bacteriological medium.

Screen for Invasive Cultures Saturated cultures of the transformed bacteria were grown at 28° C., washed twice in PBS and resuspended to a concentration of $3 \times 10^8$ bacteria $ml^{-1}$. Aliquots (50 µl) of each strain were added to monolayer cultures of HEp-2 cells seeded at a concentration of $2 \times 10^5$ animal cells per microtiter well (24 well, Falcon 3047 microtiter dishes) in RPMI1640 medium. Bacteria were centrifuged onto the monolayer at 600×g (Devenish and Schiemann, *Infect. Immun.* (1981) 32:48–55), and the infected cultures were incubated at 36° C. for 3 hours in 5% $CO_2$ atmosphere, to allow binding and invasion of bacteria. Non-adherent bacteria were removed from the monolayer by washing three times with sterile PBS, and RPMI medium containing 40 µg $ml^{-1}$ gentamicin (Sigma Chemical) was added to each microtiter well. The incubation was continued at 36° C. for 2 hours in the presence of the antibiotic, before washing the monolayers twice more with PBS. Internalized bacteria were then released from the monolayers by the addition of 1% Triton X100 and titered on L agar plates (Miller, *Experiments in Molecular Genetics*, Cold Spring Harbor Laboratory, Cold Spring Harbor, N.Y., (1972)).

The following table indicates the results.

TABLE 1

Enrichment Procedure Yields *E. Coli* Strains
That Invade Cell Culture Monolayers

| Strain | % Invasion[d] |
|---|---|
| YPIII (p⁻)[a] | 9.0 |
| HB101[b] | 0.005 |
| HB101 (pINVA2)[c] | 8.3 |
| HB101 (pINVA7) | 7.9 |
| HB101 (pINVG10) | 8.7 |
| HB101 (pRI203) | 9.2 |

[a]Yersinia pseudotuberculosis strain (Bolin et al., supra).
[b]*E. coli* K12 strain HB101.
[c]HB101 harboring cosmids denoted in parenthesis.
[d]Percentage of bacteria added to HEp-2 monolayers that resist treatment by gentamicin.

It was found that 12 of the 22 candidate strains that survived the enrichment were invasive, based on the above. It is noteworthy that the efficiency of escape from gentamicin treatment, which may be equated with bacterial invasion, was similar to that found for the *Y. pseudotuberculosis* strain used as the DNA donor.

To determine if isolated bacterial derivatives could invade cultured animal cells, ultrathin sections of monolayer cells exposed to several of the bacterial strains were analyzed by electron microscopy (Horwitz, *J. Exp. Med.* (1983) 158:1319–1331). Tissue culture cells (Falcon 3046, 6 well dishes) seeded with $8 \times 10^5$ HEp-2 cells in RPMI 1640 were incubated in the presence of $6 \times 10^{-7}$ bacteria for 3 hours at 36° C. Monolayers were then washed 10 times with PBS and incubated for 10 minutes at 37° C. in the presence of PBS containing 0.1 mM EDTA. The monolayers were gently washed once more with PBS in the presence of EDTA, suspended in 1 ml of PBS, and pelleted at 600×g for 10 minutes. The cell pellets were successively fixed with 2% glutaraldehyde and 2% osmium tetroxide in 0.1M cacodylate buffer (pH 7.4), before staining with uranyl acetate. Samples dehydrated in ethanol were embedded in Spurrs (Polysciences), thin sectioned, stained successively with 1% uranyl acetate and lead acetate (Reynolds, *J. Cell. Biol.* (1963) 17:208–213), and visualized with a Phillips 201c electron microscope. An *E. coli* K12 HB101 strain is unable to enter HEp-2 cells. In contrast, the same bacterial strain harboring an intact inv locus showed a large number of bacteria associated with the animal cell. These bacteria appeared to be both bound to the outside of the cell as well as present within large endocytic vesicles. Furthermore, when *E. coli* HB101 cells were employed which harbor the pRI203 plasmid with an intact inv locus, invasion was observed, whereas the same bacteria which harbored the plasmid pRI203.14::Tn5, which has a Tn5 insertion mutation in the inv locus were compared, no invasion was observed. Therefore, invasiveness is only observed with a functionally intact inv locus. The number of intracellular bacteria had substantially diminished and the invaded cells remained viable.

The locus of the inv gene was established as follows. One plasmid, pINVA2 was analyzed by causing a series of Tn5 insertion mutations in the cosmid DNA, taking the precaution that each mutation analyzed was the result of an independent event. Mutations were induced by the kanamycin-resistance transposon Tn5 via transposition from λb221rex::Tn5 cI857Oam23Pam80 onto pINVA2 according to the method of deBruijn and Lupski, *Gene* (1984) 27:313–149. To select for insertions onto the cosmid, kanamycin-resistant colonies were pooled together and infected lytically with λlac5 imm2lcts. The resulting lysate was used to transduce HB101 to simultaneous kanamycin- and ampicillin-resistance. Such transductants contained insertions of Tn5 at random sites on the cosmid. Several hundred such transductants were assayed for invasiveness as described previously, and the map position of 20 mutants that eliminated invasiveness and 20 insertions that had no effect on the invasive phenotype were determined. In order to ensure that each insertion was independent, the physical location of no more than one mutation from each pool was analyzed. The sensitivity to insertion inactivation of the invasive phenotype was mapped to a contiguous 3.2 kb region, which region was shown to code for a single large protein which was indicated as being 108 kdal by electrophoresis using myosin, β-galactosidase and phospholipase G as standards.

EXAMPLE 2

Demonstration of Two Genetic Loci for Invasion of Epithelial Cells in *Y. Enterocolitica*

Bacterial Strains and Tissue Culture Cells

*Y. enterocolitica* 8081c (Portnoy et al., *Infect Immun.* (1981) 31:795–782) and *E. coli* HB101 were maintained at −70° C. in Luria broth (LB) medium containing 25% (vol/vol) glycerol or on LB agar plates. Antibiotics were used at the following concentrations: ampicillin, 50 µg/ml; chloramphenicol, 50 µg/ml; kanamycin, 40 µg/ml. Human laryngeal epithelium (HEp-2), Madin-Darby canine kidney (MDCK), and Chinese hamster ovary (CHO) cells were maintained and prepared for the invasion assay as previously described (Finlay and Falkow, UCLA *Symp. Mol. and Cell. Biol.* (1987) 64:227–243). Human endometrial (HEC-1B) tissue culture cells were maintained and prepared for invasion assays in the same manner as HEp-2 cells, with the exception that 10% fetal calf serum was used in the HEC-1B tissue culture medium. *Y. enterocolitica* 8081c and *E. coli* HB101 carrying recombinant plasmids with *Y. enterocolitica* invasion genes were grown at 28° C. with aeration for 12 to 18 hours in LB. HB101 carrying the type I pilus clone PSH2 was grown in LB containing chloramphenicol at 37° C. without aeration (Orindorff and Falkow, *J. Bacteriol.* (1984) 159:736–744). HB101 carrying the PAP pilus clone pPAP5 (Hindberg et al., *EMBO J.* (1984) 3:1167–1173) was grown on tryptic soy agar plates containing ampicillin at 37° C. HB101 carrying the X-adhesion AFA-1 clone pIL14 (LabigneRoussel, *Infect Immun.* (1984) 46:251–259) was grown on LB agar plates containing ampicillin at 37° C.

Nucleic Acid Preparation and Analysis

High-molecular weight chromosomal DNA was isolated as previously described (Hull et al., *Infect Immun.* (1981) 33:933–938). Plasmid DNA was purified by the alkaline lysis method (Maniatis et al., (1982) Molecular Cloning: A Laboratory Manual, CSHL, Cold Spring Harbor, N.Y.). DNA restriction enzymes and bacteriophage T4 DNA ligase were purchased from Bethesda Research Laboratories, Inc. Calf alkaline phosphatase was purchased from Pharmacia, Inc. Restriction enzymes, ligase, and phosphatase were used according to the instructions of the manufactures.

Invasion Assay

Bacteria ($2 \times 10^7$) were added to each well of a 24-well microdilution dish which had been seeded with tissue culture cells the previous day as previously described (Finley and Falkow, (1987) supra). The microdilution plates were centrifuged for 10 minutes at ambient temperature at 162×g and then incubated in a 5% $CO_2$ incubator at 37° C. After 3 hours, the tissue culture medium was removed and the cells were washed three times with phosphate-buffered saline to remove nonadherent bacteria. Fresh tissue culture medium containing 100 μg of gentamicin per ml was then added, and the plates were reincubated as described above. After 90 minutes, the medium was removed and the cells were washed twice with phosphate-buffered saline to remove the gentamicin. The tissue culture cells were then lysed to release intracellular bacteria by adding 0.2 ml of 1% Triton X-100 to each well. After 5 minutes, 0.8 ml of LB was added; the final concentration of Triton X-100 was 0.2%. The suspension was then diluted and plated on the appropriate bacteriological medium to determine viable counts. Viable counts of the initial bacterial culture were also determined. Results are expressed as follows:

% invasion=100×(the number of bacteria resistant to gentamicin/ the number of bacteria added).

The total number of cell-associated bacteria was determined in the same way as was the number of intracellular bacteria, with the following exception: after incubation of the bacteria with the monolayer for 3 hours, the monolayer was washed five times with phosphate-buffered saline. The monolayer was then disrupted with 1% Triton X-100 as described above, and viable counts were determined.

Construction of a Chromosomal DNA Library of *Y. enterocolitica*

High-molecular-weight chromosomal DNA from *Y. enterocolitica* 8081c was partially digested with the restriction enzyme Sau3A as previously described (Maniatis et al., (1982) supra). Fragments 7 to 10 kilobase pairs in size were isolated by sucrose gradient fractionation and ligated into pBR322 that had been digested with BamHI and treated with calf alkaline phosphatase. The resulting ligated DNA was used to transformcompetent *E. coli* HB101 cells. *E. coli* HB101 transformants carrying recombinant plasmids were selected on LB agar plates containing ampicillin.

Stained Samples and Electron Microscopy

Samples of invasion assays were prepared and stained for electron microscopy as previously described (Isberg and Falkow, *Nature* (1985) 317:262–264).

Tn5 Mutagenesis

Strains bearing insertions of transposon Tn5 into recombinant plasmid pVM102 were isolated as previously described (deBruijn and Lupski, *Gene* (1984) 27:131–149).

Cloning Invasion Genes from *Y. enterocolitica*

*Y. enterocolitica* 8081c (serotype 08) was used, which had been isolated from a patient with septicemia, as our prototype strain (Portnoy et al. (1981) supra). Strain 8081c lacks the 47-megadalton virulence-associated plasmid, as well as any other plasmid, yet is still able to invade HEp-2 cells as efficiently as is the plasmid-containing strain. This suggests that, as in *Y. pseudotuberculosis*, the invasion determinants are chromosomally encoded. Consequently, to clone the genes from *Y. enterocolitica* 8081c which were involved in invasion, a library of chromosomal DNA from strain 8081c, was first constructed in the plasmid vector pBR322. This library was used to transform the normally nonadherent and noninvasive *E. coli* HB101. Adhesive and invasive clones were selected by pooling the resulting transformants and infecting a monolayer of HEp-2 tissue culture cells as described above in Materials and Methods. After 3 hours of incubation, the monolayer was washed 15 times with phosphate-buffered saline and then lysed with 1% Triton X-100 to release any intracellular or adherent bacteria. The suspension was then spread on LB plates containing ampicillin. Gentamicin was not used during this enrichment procedure because we felt that invasion may be a two step process involving at least two loci, one for attachment and a second for invasion. If this were the case, the attachment factor would be a prerequisite for identifying a recombinant strain carrying the invasion gene.

Clones from the enriched population were then tested individually in the invasion assay. Approximately 50% of the clones that survived the enrichment were able to invade HEp-2 tissue culture cells to some degree.

*E. coli* HB101 transformants expressing an invasion phenotype fell into two classes (Table 2). The first class, represented by clones 6, 8, and 9, demonstrated a high level of invasion similar to that of wild-type *Y. enterocolitica* 8081c and 800- to 1,400-fold higher than the background level seen with *E. coli* HB101. The second class, represented by clones 3 and 7, demonstrated a relatively low level of invasion, which was nevertheless 40- to 100-fold higher than that of HB101.

TABLE 2

Relative Invasion of *Y. enterocolitica* Clones Into HEp-2 Cells*

| Infecting Strain | % Invasion |
| --- | --- |
| *Y. enterocolitica* 8081c | 26.8 ± 3.6 |
| *E. coli* HB101 | 0.0075 ± 0.0035 |
| HB101 (pBR322-8081c) (clone 3) (= pVM103) | 0.82 ± 0.24 |
| HB101 (pBR322-8081c) (clone 7) (= pVM102) | 0.37 ± 0.19 |
| HB101 (pBR322-8081c) (clone 6) (= pVM101) | 6.2 ± 2.1 |
| HB101 (pBR322-8081c) (clone 8) | 10.8 ± 0.1 |
| HB101 (pBR322-8081c) (clone 9) | 6.9 ± 0.32 |

*Strains were used to infect a monolayer of HEp-2 tissue culture cells as described in Materials and Methods. Values are the averages of duplicate samples, with the ranges indicated, and reflect similar results from several experiments.

Characterization of *Y. enterocolitica* Invasion Clones

Isolation and characterization of plasmid DNA from clones 6, 8, and 9 indicated that they all contain the same fragment of *Y. enterocolitica* DNA. The recombinant plasmid from clone 6 was called pVM101. Southern hybridization analysis indicated that plasmid pVM101 shares homology with the inv gene from *Y. pseudotuberculosis* and thus is a clone of the *Y. enterocolitica* inv locus. The homology shared with *Y. pseudotuberculosis* inv is not observed at the restriction map level.

Isolation and characterization of plasmid DNA from clones 3 and 7 indicated that they have overlapping inserts of *Y. enterocolitica* DNA. These two plasmids were renamed pVM103 and pVM102, respectively. Plasmids pVM102 and pVM103, while they share homology with each other, are not homologous to pVM101, as demonstrated by both Southern hybridization and restriction map analysis and thus probably represent a new locus involved in invasion.

A high proportion of *E. coli* HB101 recombinant cells carrying either pVM102 or pVM103 adhered to the HEp-2 cell monolayers. This raised the possibility that the low level of invasion observed with the quantitative invasion assay reflected a small proportion of adherent bacteria that were protected from the gentamicin treatment. To determine whether bacteria were actually being internalized, electron microscopy was performed on samples of HEp-2 cells infected with HB101(pVM102). Bacteria were frequently found in very close association with eucaryotic cell membranes. A small number of intracellular bacteria were also observed suggesting that pVM102 confers a phenotype of adhesion and low-level invasion of HEp-2 tissue culture cells on *E. coli* HB101. Electron-dense eucaryotic structures resembling coated pits were frequently found in association with attached bacteria, regardless of whether the bacteria were *Y. enterocolitica* 8081c or *E. coli* HB101 carrying either of the recombinant plasmids, pVM101 or pVM102.

Whether or not these structures play a role in microbial attachment or entry or both is not known at this time. Strain 8081c, unlike HB101 carrying either pVM101 or pVM102, is seen almost exclusively intracellularly after 3 hours of infection. This observation would suggest either that there are other gene products directly involved in invasion or that the gene products encoded by pVM101 and pVM102 do not function as effectively in an *E. coli* background. Electron microscopy of negatively stained cultures of HB101 pVM102 and pVM101 do not indicate the presence of any pilus-like structures on the surface of these bacterial cells.

The ability of *E. coli* HB101 carrying several cloned virulence-associated adhesions to invade HEp-2 cells was tested (Table 3) to determine whether adherence alone promoted a low level of invasion. HB101 harboring recombinant plasmids encoding type 1 pili (Orndorff and Falkow, (1984) supra), PAP pili (Lindberg et al., (1984) supra), or X-adhesion AFA-1 (Lahyne-Roussel et al., (1984) supra) was cultured in such a way as to maximize expression of the adhesion. While all three of these adhesions promoted adherence of *E. coli* HB101 to HEp-2 cells, as determined by examination of Giemsa-stained cover slips and by quantitative assay, the presence of type 1 pili, PAP pili, or X-adhesion did not confer an invasive phenotype of *E. coli* HB101 (Table 3), nor were coated pits seen associated with the adherent bacteria. This result indicates that the invasive phenotype of HB101(pVM102) is a specific property of this recombinant strain and not a manifestation of simple adhesion.

TABLE 3

Effect of Adhesion on Invasions[a]

| *E. coli* Strain | % Invasion | Adhesion Type |
| --- | --- | --- |
| HB101 (pBR322) | 0.015 ± 0 | —[b] |
| HB101 (pVM102) | 0.770 ± 0.03 | — |
| HB101 (pSH2) | 0.067 ± 0.001 | Type 1 pilus |
| HB101 (pPAPS) | 0.020 ± 0 | PAP pilus |
| HB101 (pIL14) | 0.007 ± 0.001 | X-adhesion |

[a]Strains were used to infect a monolayer of HEp-2 tissue culture cells as described in Materials and Methods. Values are the averages of duplicate samples, with the ranges indicated, and reflect similar results from several experiments.
[b]—, not known.

Localization of the Invasion Locus of pVM102

Insertions of transposon Tn5insertions were mapped, and their invasive phenotypes were determined. Six insertions that eliminated invasion were clustered to the right of the unique ClaI site. Insertion mutants defective for invasion were found only in this region, suggesting that there is only one region on this plasmid that is responsible for both adherence and invasion. There are only approximately 650 base pairs between the Inv+ insertions flanking the Inv-- insertions, suggesting that this region contains a very small gene(s). We have designated this region ail for attachment-invasion locus.

Invasion of Other Tissue Culture Cell Lines

One possibility for the role of ail gene(s) is that it defines target cell types other than those defined by inv, thus giving *Y. enterocolitica* a different range of target host cells than might result from the presence of inv alone. To test this hypothesis, invasion by HB01 carrying either of the cloned *Y. enterocolitica* invasion loci, inv or ail, was examined in several cell lines (Table 4). All cell lines were invaded by *Y. enterocolitica* 8081c, although to various degrees. Plasmid pVM101 promoted only a low level of invasion of MDCK cells by HB101. Plasmid pVM101 caused HB101 to invade all tested cell lines, except the MDCK cells, at a relatively high level. HB101(pVM102) invaded the tested cell lines to different degrees. The recombinant strain HB101(pVM102) did not invade MDCK cells, invaded HEp-2 and HEC1B cells at a low level, and invaded CHO cells at a high level. This suggests that cell lines may vary in their capacity to phagocytize bound bacteria and that this variability can be specific to the invasion factor expressed by the bacteria.

TABLE 4

Invasion of Tissue Culture Cell Lines by
Y. enterocolitica and Y. enterocolitica Bacteria in Tissue Culture Cell lines[a]

| Infecting Strain | % Invasion Of: | | | |
|---|---|---|---|---|
| | HEp-2 | MDCK | CHO | HEC1B |
| 8081c | 26.8 ± 3.6 | 0.93 ± 0.07 | 20.4 ± 5.9 | 124.3 ± 5.0 |
| HB101(pBR322) | 0.0075 ± 0.0035[b] | <0.0001 | 0.08 ± 0.01 | 0.005 ± 0.001 |
| HB101 (pVM101) | 6.2 ± 2.1 | 0.015 ± 0.0015 | 15.2 ± 1.3 | 19.1 ± 2.4 |
| HB101 (pVM102) | 0.37 ± 0.19 | <0.0001 | 12.7 ± 0.2 | 5.5 ± 1.2 |

[a]Strains were used to infect monolayers of the tissue culture cell lines as described in Materials and Methods. Values are the averages of duplicate samples, with the ranges indicated, and reflect similar results from several experiments.
[b]From infection of HEp-2 with HB101. Results were similar for HB101 and HB101 (pBR322).

The total number of cell-associated bacteria, both attached and intracellular, was also determined (Table 5). Although HB101 (pVM102) invaded HEp-2 cells at only a low level, it bound to HEp-2 cells as well as if not better than it did to CHO cells and to a slightly higher degree to both these cell lines than did HB101(pVM101) (Table 5). Indeed, there is no correlation between number of bacteria bound and number of bacteria internalized, suggesting that the interaction of these bacteria with tissue culture cells that leads to internalization involves more than just attachment to the cell surface.

TABLE 5

Parent Cell-Associated Bacterial in Tissue Culture Cell Lines[a]

| Infecting Strain | % Invasion of | | | |
|---|---|---|---|---|
| | HEp-2 | MDCK | CHO | HEC1B |
| 8081c | 67.0 ± 4.0 | 15.0 ± 1.7 | 51.0 ± 5.0 | 104.0 ± 53 |
| HB101 (pBR322) | 11.0 ± 1.7 | 0.34 ± 0.07 | 3.6 ± 0.71 | 7.4 ± 2.3 |
| HB101 (pVM101) | 34.0 ± 2.0 | 4.4 ± 0.05 | 26.0 ± 3.0 | 58.0 ± 5.2 |
| HB101 (pVM102) | 43.0 ± 0.2 | 4.2 ± 0.2 | 37.0 ± 4.0 | 10.0 ± 1.6 |

[a]Strains were used to infect monolayers of the tissue culture cell lines as described in Materials and Methods. Values are the averages of duplicate samples, with the ranges indicated, and reflect similar results from several experiments.

The above results demonstrate that the invasion loci, designated inv, allows a uniformly high level of invasion in several tissue culture lines and the inv gene of Y. pseudotuberculosis and Y. enterocolitica are homologous. The second invasion locus of Y. enterocolitica is ail. Bacteria containing ail exhibit several invasion phenotypes, depending upon which cell line is infected. ail promotes a high level of invasion of CHO cells and a low to moderate level of invasion of other cell lines (HEp-2 and HEC-1B) but allows no invasion of MDCK cells. The recombinant plasmid pVM102 strongly promotes adherence of E. coli HB101 to many cell lines, including those cell lines for which it does not promote efficient invasion (e.g., HEp-2). Although E. coli (pVM102) adheres as well to HEp-2 cells as to CHO cells, more intracellular bacteria are found in CHO cells. The phenotypes of attachment and invasion which are associated with the presence of pVM102 appear to be encoded by fewer than 650bp of DNA.

EXAMPLE 3

Screening of Yersinia for Pathogenesis Materials and Methods

Bacterial Strains and Tissue Culture Cells

Bacterial strains were maintained at −70° C. in Luria broth (LB) medium containing 25% (vol/vol) glycerol, or on LB agar plates. Yersinia strains obtained from a variety of sources were tested for invasion in the tissue culture assay (TCI phenotype) and hybridization to the probes described below without prior knowledge of their serotype or source to ensure an unbiased evaluation. E. coli strain HB101 (FhsdS20 ($r_B$-,$m_B$-) recA13 ara14 proA2 lacY1 galK2 rpsL20 xY15 mtl1) (Bachman, Bacteriol. Rev. (1972) 36:525–557) carrying the recombinant plasmids pRI203, pVM101, or pVM103 were maintained on LB agar plates containing 50 µg/ml ampicillin (Ap). Human laryngeal epithelial (HEp2) cells were maintained and prepared for the invasion assay as previously described (Finlay and Falkow, (1987) supra). Yersinia strains were grown at 28° C. with aeration for 12 to 18 hours in LB for the invasion assays.

Nucleic Acid Purification and Probe Preparation

Chromosomal DNA was isolated as described (Mekalanos, Cell (1983) 35:253–263). Plasmid DNA was purified by a cleared lysate method followed by CsCl equilibrium density centrifugation as described (Maniatis et al., (1982) supra). DNA restriction enzymes were purchased from Bethesda Research Laboratory, and were used according to the instructions of the manufacturer. DNA probes were prepared as follows. Plasmid DNA was digested with the appropriate restriction endonucleases, and the fragments were separated by electrophoresis through a 0.7% agarose gel. The DNA fragments were purified from the agarose gel slices using Geneclean (Bio101, La Jolla, Calif.). The purified fragments were then labelled with $^{32}P$ by nick translation for use as probes as previously described (Maniatis et al., Proc. Natl. Acad. Sci. U.S.A. (1975) 72:1184–1188).

Southern Hybridization Analysis

Chromosomal DNA was digested to completion with EcoRV, and the fragments were separated by electrophoresis through a 0.7% agarose gel. The separated DNA fragments were transferred to nitrocellulose (Schleicher & Schuell, Keene, N.H.) as described by Southern. Hybridizations were performed at either medium or low stringency. Medium stringency conditions were as follows: the filter is prehybridized for 1 hour at 37° C. in 35% formamide/4×SSC/ 0.1% SDS/1 mM EDTA/1×Denhardts.

The prehybridization solution is then removed and hybridization solution (same as prehybridization solution)

containing 250 μg/ml calf thymus DNA and the boiled probe is added to the filter. After hybridization for 12 to 18 hours at 37° C. the filter was washed three times with 5×SSC/0.1% SDS at 65° C. for 15 minutes, 10 minutes, and 5 minutes. Then the filter was washed in 2×SSC at room temperature for 5 minutes, air dried, and exposed to Kodak XAR-5 film. Low stringency conditions are the same as medium stringency except that 20% formamide is used in the prehybridization and hybridization solutions. The filters can be reused if washed in 0.25M NaOH at room temperature for 6 to 10 hours, and rinsed briefly in 2×SSC. Probe results presented for a given strain were obtained using a single filter that was reprobed several times. This allowed direct comparison of fragments that hybridized to the various probes used.

Colony blots were hybridized as above. Individual colony blots were used for each probe rather than rehybridizing the same filter.

Tissue Culture Invasion Assay (TCI)

Either quantitative or qualitative TCI assays were performed. The quantitative assay is as follows: bacteria (approximately $2\times10^7$) were added to each well of a 24 well microtiter plate which had been seeded with tissue culture cells the previous day as described (Finlay and Falkow, (1987) supra). The microtiter plates were centrifuged for 10 minutes/162×g/ambient temperature, and then incubated in 5% $CO_2$ at 37° C. After 90 minutes the tissue culture medium was removed, and the cells were washed three times with phosphate buffered saline (PBS) to remove non-adherent bacteria. Fresh tissue culture medium containing 100 μg/ml gentamicin was then added, and the plates were reincubated as above. After 90 minutes the medium was removed, and the monolayers were washed twice with PBS to remove the gentamicin. The tissue culture cells were then lysed to release intracellular bacteria with 0.2 ml of 1% Triton X-100. After five minutes, 0.8 ml of LB was added bringing the final concentration of Triton X-100 to 0.2%. The suspension was then diluted and plated on the appropriate bacteriological medium to determine viable counts. Viable counts of the initial bacterial culture were also determined. Results are expressed as follows:

% invasion=100×(# bacteria resistant to gentamicin/# bacteria added)

The qualitative assay was performed as described above. After washing twice with PBS to remove the gentamicin, the tissue culture cells were lysed to release intracellular bacteria by adding 0.2 ml of 1% Triton X-100 to each well. After five minutes, 0.8 ml of LB was added. Fifty microliters of this suspension was then spread on an LB agar plate. Results are scored as either TCI+ or TCI–. TCI+ strains give almost confluent growth on the LB plate after the assay, whereas TCI– strains give a few isolated colonies.

TCI Phenotype

One hundred seventy-seven *Yersinia* strains were examined for their TCI phenotype (1 *Y. pestis,* 10 *Y. pseudotuberculosis* 149 *Y. enterocolitica,* 4 *Y. frederiksenii,* 4 *Y. kristensenii,* 3 *Y. intermedia,* 2 *Y. aldovae,* 4 new species 9). These strains were isolated in a variety of geographical locales and over a time span of more than ten years; nine of the *Y. enterocolitica* strains were isolated from four outbreaks and thus probably represent only four distinct isolates. Twenty-six different serotypes are represented. Forty strains were examined quantitatively and qualitatively. Values for TCI+ strains using the quantitative assay ranged from 0.6% to 7.8%; values for TCI– strains ranged from 0.014% to 0.023%. In all cases there was at least a 26-fold difference between the TCI+ and TCI– strains. Thereafter the qualitative TCI assay was used. No strain gave ambiguous results; even strains that exhibited extensive cytotoxic activity were still clearly invasive. The results observed indicate that serotypes that are commonly found in the clinical setting were TCI+, whereas serotypes commonly isolated from the environment were TCI–. This result is in agreement with previous studies that have observed a good correlation between potential pathogenicity, as defined by serotype, and the ability to invade tissue culture cells (Lee et al., *Can. J. Microbiol.* (1977) 23:1714–1722; Schieman and Denenish, *Infect. Immun.* (1982) 35:497–506).

Probes

Four different probes were used in the experiments. The Inv-Ent probe was a 3.6 kb ClaI fragment purified from pVM101. This probe contained most of the inv gene from *Y. enterocolitica* in addition to adjacent sequences; it is known that DNA to the left of the EcoRV site is not required for inv activity. The Inv-Pstb probe was a 2.4 kb ClaI-XhoI fragment purified from pRI203 (Isberg et al., *Cell* (1987) 50:769–778). This fragment contained only sequences internal to the *Y. pseudotuberculosis* inv gene. Although Southern blot analysis indicated *Y. enterocolitica* and *Y. pseudotuberculosis* inv genes were homologous, no similarity was observed in their restriction maps. Both these inv genes promote a high level of invasion by *E. coli* HB101 of a variety of tissue culture cell lines.

Two probes were used from the *Y. enterocolitica* ail locus, AIL-B and AIL-C. AIL-B was a 900 bp AvaI-ClaI fragment from pVM103. AIL-C was a 1.2 kb ClaI-AvaI fragment from pVM103. Genetic analysis with the transposon Tn5 had indicated that DNA contained within the AIL-C probe was required for the Ail phenotype. No Tn5 insertions eliminating the Ail phenotype have been isolated in AIL-B. Preliminary DNA sequence data suggests that only six base pairs of the ail coding sequence are located within AIL-B; the remainder of the ail coding sequence is contained within AIL-C.

Most blots were also probed with labelled pBR322 (the cloning vector). Although some strains clearly had homology to pBR322, the hybridizing fragments were different from those hybridizing to the inv or ail probes.

Location of inv and ail

The inv and ail genes were cloned from *Y. enterocolitica* strain 8081c. Strain 8081c lacks detectable plasmid DNA and plasmid associated phenotypes, but it is possible that the plasmid has integrated into the chromosome. To determine if inv and ail are truly chromosomal genes rather than plasmid genes Southern analysis was performed of purified virulence plasmid DNA and chromosomal DNA from strain 8081c. None of the probes hybridized to the plasmid DNA indicating that the inv and ail genes are not located on the plasmid. The restriction endonuclease used to digest the DNA (EcoRV) cuts once within the Inv-Ent probe so two fragments from chromosomal DNA were found that hybridized to the Inv-Ent probe. The AIL-C probe hybridized to a single fragment from chromosomal DNA, but the AIL-B probe hybridized to several chromosomal DNA fragments. The restriction endonuclease used (EcoRV) does not cut within the AIL-B probe, therefore a sequence present within AIL-B is repeated within the chromosome. Although there are indications that the virulence plasmid may contain a repeated sequence, it appears to be distinct from the repeated sequence identified by the AIL-B probe. The results also indicate that inv and ail are probably single copy loci and, because probes derived from these genes hybridize to different fragments, are not adjacent to each other on the chromosome.

Hybridization of AIL-C to DNA from *Y. enterocolitica* Strains

Many non-pathogenic strains of *Y. enterocolitica* were TCI–. We supposed they might be missing essential genes required for invasion, or they might contain the appropriate gene in a nonfunctional form. To investigate if these possibilities pertained to ail or inv we did either Southern or colony blot analysis of the 149 *Y. enterocolitica* strains. The AIL-C probe did not hybridize to DNA from all strains. If one compares hybridization to AIL-C and the TCI phenotype one finds that 85 of 86 TCI+ strains had homology to AIL-C, whereas only 1 of 63 TCI– strains had homology to AIL-C. Thus there was a better than 98% correlation between the AIL-C and TCI phenotypes. This result supports the hypothesis that the ail locus encodes a virulence factor (s).

Hybridization to AIL-B to DNA from *Y. enterocolitica* Strains

The AIL-B probe like the AIL-C probe did not usually hybridize to TCI– strains. However, the TCI+ strains can be divided into two distinct groups—those that showed strong hybridization to AIL-B, and those that showed weak or no hybridization to AIL-B. Strains which hybridized strongly to AIL-B always had multiple fragments that hybridized; the number and size of these fragments varied from strain to strain. Strains which hybridized only weakly to AIL-B always had only one fragment that hybridized. This fragment was usually identical to the fragment that hybridized to AIL-C. Preliminary sequencing results indicate that the ail coding region extends only 6 bp into AIL-B. This suggests that the weak hybridization seen to AIL-B in these strains could be due to a short sequence associated with ail, but that these strains lack sequences present in AIL-B that are repeated in the chromosome of strains that hybridize strongly to this probe.

TCI+ strains that hybridized strongly to AIL-B include the serotypes 013a,13b; 018; 020; 021; 04; 04,32; 04,33; and 08. TCI+ strains that hybridize weakly or not at all to AIL-B include the serotypes 01,2,3; 03; 05,27; and 09. Interestingly this represents a clean division between the pathogenic "American" serotypes (i.e., those isolated only in North America), and other pathogenic serotypes isolated in Europe, Japan, Southern Africa, and Canada with regard to AIL-B phenotype. Although both groups of potentially pathogenic serotypes have the ail gene, the non-"American" strains appear to lack a sequence located near ail that is found repeated in the chromosome of "American" strains.

Hybridization of Inv-Ent and Inv-Pstb to DNA from *Y. enterocolitica* Strains

The Inv-Ent probe hybridized to DNA isolated from all strains, nevertheless there were differences between pathogenic and non-pathogenic strains. We observed several distinct hybridization patterns. We have labelled them type I, II, I/II, III, IV, and V. Type I strains had 9.5 kb and 4.0 kb fragments, and type II had 9.7 kb and 3.8 kb fragments, that hybridized to the Inv-Ent probe. There were 36 strains that were type I, of these 34 were TCI+. Type I/II shared a 9.7 kb fragment with Type II and a 4.0 kb fragment with type I; all six type I/II strains were TCI+. The remaining four groups, II, III, IV, and V were all TCI–. Type V shared a 9.5 kb fragment with type I and in addition had a 5.0 kb fragment that hybridizes to Inv-Ent. The hybridization of Inv-Ent to type III was weak relative to the hybridization observed with other strains. The type III pattern appears identical to the hybridization pattern observed for *Y. intermedia*. Type IV is a catch-all for strains with unique hybridization patterns. Overall there was a correlation between strains that are TCI+ and the type I or I/II hybridization pattern, while strains that were TCI– exhibit type II, III, IV, or V hybridization patterns.

Unlike the Inv-Ent probe, the Inv-Pstb probe contained only inv coding sequence. Therefore fragments that hybridized to Inv-Pstb were those with sequences related to the inv gene itself. The Inv-Pstb probe hybridized to all *Y. enterocolitica* strains tested except for the type III strains. In each case the fragment that hybridizes to Inv-Pstb is identical to one of the fragments recognized by Inv-Ent. InvPstb hybridized to the 9.5 kb fragment of types I and V, and to the 9.7 kb fragment of types II and I/II. This result indicates that the hybridization of Inv-Ent to these fragments probably represents homology to inv sequences. Hybridization of Inv-Ent to other fragments is probably due to homology to DNA sequences adjacent to inv. The results using the Inv-Pstb probe also suggest that type III strains do not have an inv gene and that the hybridization observed with the Inv-Ent probe is due to sequences adjacent to inv. Alternatively, but less likely, the type III strains have diverged more from the *Y. pseudotuberculosis* inv gene than have other *Y. enterocolitica* strains. As mentioned above the type III hybridization pattern is like that seen for *Y. intermedia* strains, so it is possible that these strains have been incorrectly speciated.

Hybridization Phenotypes of Strains Isolated During Several Outbreaks

As noted above, there is an extremely good correlation between the ability to invade tissue culture cells and hybridization to the inv and ail probes. Is a similar correlation seen between *Y. enterocolitica* strains that clearly caused clinical disease and hybridization to the probes? To address this question we examined strains previously characterized from outbreaks of yersiniosis. The strains examined included those isolated from patients and those isolated from asymptomatic individuals at the same time in the same region. The data indicate that all *Y. enterocolitica* isolates that are strongly implicated as the cause of disease were TCI+, whereas strains isolated from asymptomatic individuals were either TCI– or TCI+. As were other TCI+ strains, these strains were type I with the Inv-Ent probe. A strain isolated from an asymptomatic family member of a patient was TCI– and was type II with the Inv-Ent probe.

The strains isolated from patients are AIL-C+ and AIL-B+. The TCI– strains were AIL-B– and AIL-C– as was previously observed for other TCI– strains. The pattern of hybridization of AIL-B to DNA from random *Y. enterocolitica* isolates varied from strain to strain. However, strains isolated from the same outbreak exhibited identical hybridization patterns to the AIL-B probe. This probe may, therefore, serve as a useful marker for identifying the source, and following a particular epidemic.

Presence of inv and ail Sequences Among the Yersiniae

Three species of *Yersinia* are generally recognized as pathogenic for animals: *Y. pestis*, *Y. pseudotuberculosis*, *Y. enterocolitica*. Several other *Yersinia* species have been defined, but these are generally considered to be non-pathogenic. Are the differences observed, using the inv and ail probes, between pathogenic and non-pathogenic *Y. enterocolitica* also true for the genus *Yersinia* as a whole? DNA isolated from all species of *Yersinia* tested exhibited homology to the Inv-Ent probe, but only the pathogenic species showed strong homology to the Inv-Pstb probe. The DNA fragments hybridizing to Inv-Pstb and Inv-Ent for *Y. pestis*, *Y. pseudotuberculosis*, and *Y. enterocolitica* were the same, suggesting these fragments encode the inv gene. In contrast, *Y. aldovae*, *Y. intermedia*, *Y. frederiksenii*, *Y. kristensenii*, and new species 9 showed only very weak hybridization to Inv-Pstb, and the fragments hybridizing to Inv-Pstb were not the same as those hybridizing to Inv-Ent, suggesting the hybridization to Inv-Ent may be due to sequences present in the probe adjacent to inv rather than to inv itself.

The AIL-B and AIL-C probes both hybridized to DNA isolated from *Y. pestis*, and *Y. pseudotuberculosis* as well as to pathogenic *Y. enterocolitica*. The fragments that hybridized to these two probes differed though, indicating either that the AIL-B and AIL-C sequences are separated on the chromosome of these species (unlike *Y. enterocolitica*), or that an EcoRV site separates these sequences. The AIL-B probe hybridized strongly to only one DNA fragment in *Y. pestis* and *Y. pseudotuberculosis* strain YPIII, but after longer exposure several additional weak hybridization signals could be observed for *Y. pestis*. DNA isolated from twenty-three different species in addition to the *Yersinia* spp. was also examined for hybridization to these probes using low stringency conditions. No hybridization to the Inv-Ent probe was observed, suggesting this probe contains *Yersinia* specific sequences. No hybridization to the AIL-C probe was observed either, suggesting this probe contains DNA sequences specific to pathogenic *Yersiniae*. Only DNA isolated from a strain of *Klebsiella pneumonia* hybridized to AIL-B; four hybridizing fragments were observed when digested with the restriction endonuclease EcoRV, suggesting the sequence is repeated in *Klebsiella pneumonia* as it is in *Y. enterocolitica*.

Hybridization of inv and ail to *Y. pseudotuberculosis*

As noted above, all four probes used in this study hybridized to DNA isolated from *Y. pseudotuberculosis* strain YPIII. To determine if this is generally true we examined nine other *Y. pseudotuberculosis* strains isolated from both humans and animals. All of these strains were TCI+ and hybridized to all probes. Two different hybridization patterns were observed with the Inv-Pstb probe, but there was no obvious correlation between serotype or source, and hybridization pattern. In addition to the fragment that hybridized to AIL-B in all strains, a few strains also show four other weakly hybridizing fragments; these fragments are the same for all strains that exhibit the phenotype. Although only a few *Y. pseudotuberculosis* strains were examined it appears that the species *Y. pseudotuberculosis* is more homogenous with regard to the inv and ail loci than is *Y. enterocolitica*.

The above results demonstrate that tissue culture invasiveness is a good indicator of potential pathogenicity. This has been proposed in several other studies. Lee, *Contr. Microbiol. Immunol.* (1979) 5:228–233; Lee et al., *Can. J. Microbiol.* (1977) 23:1714–1722; Schiman and Devenish, *Infect. Immun.* (1982) 35:497–506; and Une, *Microbiol. Immunol.* (1977) 21:365–377. Strains strongly implicated as the cause of outbreaks of gastrointestinal disease are exclusively TCI+, and strains isolated from healthy individuals at the same time and locale as strains associated with disease are often TCI–. These results support the hypothesis that tissue invasiveness is an important aspect of *Yersinia* pathogenesis and that the ability to invade tissue culture cells is a good in vitro assay for the invasive ability of virulent strains.

EXAMPLE 4

The following describes the identification of the ail gene analog in *S. typhimurium*.

Strains and Media

All rich media was Luria broth (LB) and all minimal media was M9 (Davis et al., (1980) *Advanced Bacterial Genetics*, Cold Spring Harbor Lab, Cold Spring Harbor, N.Y. p.21). The construction of *S. typhimurium* strain CS119 pagC1::TnphoA phoN2 zxx::6251 Tn10d-Cam was previously described (Fields et al., (1989) *Science* 243:1059–1062) American Type Culture Collection (ATTC) *S. typhimurium* strain 10428 was the wild-type parent of CC119. Other strains derived from ATCC 10428 included CS018 which is isogenic to CS119 except for phoP105::Tn10d CS022, phoP-24 (Con) (Miller and Mekalanos (1989) *J. Bacteriol;* Fields et al., (1989) supra), and CS015 phoP102::Tn10d-Cam. Other wild-type strains used for preparation of chromosomal DNA included *S. typhimurium* LT2 (ATCC 15277), *S. typhimurium* Q1 and *S. drypool* (Dr. J. Peterson U. Texas Medical Branch, Galveston), and *Salmonella typhi* Ty2 (Dr. Caroline Hardegree, Food and Drug Administration). AP activity was screened on solid media using the chromogenic phosphatase substrate 5-bromo-4-chloro-3-indolyl phosphate, (XP). AP assays were performed as previously described and are reported in units as defined by Miller ((1972) Experiments in Molecular Genetics, Cold Spring Harbor Lab, Cold Spring Harbor, N.Y. pp. 352–355.

Protein Electrophoresis and Western Blot Analysis

One dimensional protein gel electrophoresis was performed by the method of Laemmli and blot hybridization using antibody to AP was performed as previously described (Peterson and Mekalanos (1988) *Infect. Immun.* 56:2822–2829). Whole cell protein extracts were prepared from saturated cultures grown in LB at 37° C. with aeration, by boiling the cells in SDS-PAGE sample buffer (Laemmli (1970) *Nature* 227:680–685). Two dimensional gel electrophoresis was performed by the method of O'Farrell. Proteins in the 10% polyacrylamide slab gels were visualized by silver staining (Meril et al., (1984) *Meth. in Enzymology* 104:441)

DNA analysis and sequencing

Chromosomal DNA was prepared by the method of Mekalanos ((1983) *Cell* 35:253–263). DNA, size fractionated in agarose gels, was transferred to nitrocellulose (for blot hybridization) by the method of Southern ((1975) *J. Mol. Biol.* 98:503–517). DNA probes for Southern hybridization analysis were radiolabeled by the random primer method (Feinberg and Vogelstein (1984) *Anal. Biochem.*). Plasmid DNA was transformed into *E. coli* and *Salmonella* by calcium chloride and heat shock (Machlachlan and Sanderson (1985) *J. Bacteriol.* 161:442–445), or by electroporation using a Genepulser apparatus (Biorad) as recommended by the manufacturer (Domer et al., (1988) *Nucl. Acids Res.* 16:6127–6145). DNA sequencing was performed by the dideoxy chain termination method of Sanger as modified for use with Sequenase (U.S. Biochemical). Oligonucleotides were synthesized on an Applied Biosystems machine and used as primers for sequencing reactions. Specific primers unique to the two ends of Tn PhoA, one of which corresponds to the alkaline phosphatase coding sequence and the other to the right IS50 sequence were used to sequence the junctions of the transposon insertion.

RNA Purification and Analysis

RNA was purified from early log phase *Salmonella* cultures by the hot phenol method (Case et al., *Gene* 72:219–236), and run in agarose-formaldehyde gels for blot hybridization analysis (Thomas (1980) *PNAS U.S.A.* 72:5201).

Identification of an 18 kDa Protein Missing in a PagC Mutant of *S. typhimurium*

Strain CS119 was analyzed by two dimensional protein electrophoresis to detect protein species that might be absent as a result of the TnphoA insertion. Identification of multiple changes in the protein profile of CS119 relative to the parent strain supports that the expression of a large operon or a regulatory locus was altered as a result of the transposon insertion. Only a single change in protein species was observed when strains, isogenic except for their transposon insertions, were subjected to this analysis. A single protein of approximately 18 kilodaltons (kDa) and pI of approximately 8.0 is missing in the strain with the pagC::TnphoA insertion. This 18 kDa species is also missing in *Salmonella* strains with mutations in phoP and phoO. The size and pI of this protein was similar to that predicted to be disrupted by insertion of TnphoA into pagC.

Analysis of the PagC-AP Fusion Protein

Western blot analysis using antibody to AP was performed to determine the size of the AP fusion protein produced by strain CS119 and to determine the amount of *S. typhimurium* DNA sequence needed to encode the fusion protein. The PagC-AP fusion protein is similar in size to native alkaline phosphatase at 45 kDa, indicating that either a small coding sequence of *Salmonella* DNA is contributing to the gene fusion, or a large unstable fusion is produced. The lack of production of the 45 kDa PagC-AP fusion protein in strain CS018, isogenic to strain CS119 except for a phoP::Tn10d insertion, further demonstrates the dependence on an intact phoP locus for efficient expression of pagC.

Cloning of the pagC::TnphoA Insertion

Chromosomal DNA was prepared from *S. typhimurium* strain CS119 and Southern hybridization analysis was performed using a gene fragment from TnphoA as a probe. This fragment hybridizes preferentially to one end of TnphoA if the restriction enzyme BamHI is used in the analysis (Peterson and Mekalanos (1988) supra). Therefore, a number of double restriction endonuclease digestions including BamH1 were used to determine a rough physical map of the restriction endonuclease sites in the region of the pagC::TnphoA fusion. This analysis indicated that digestion with the restriction endonucleases XbaI and EcoRV yielded a single DNA fragment that included the pagC::TnphoA insertion in addition to several kilobases of flanking DNA. Therefore, chromosomal DNA from strain CS119 was digested with XbaI and EcoRV and ligated into the bacterial plasmid vector pUC19 that had been digested with the restriction endonucleases XbaI and SmaI. This DNA was electroporated into the *E. coli* strain DH5-alpha and colonies were plated onto LB agar containing the antibiotics kanamycin (TnphoA encoded) and ampicillin (pUC19 encoded). A single ampicillin and kanamycin resistant clone containing a plasmid designated pSM100 was selected for further study.

A radiolabeled DNA probe from pSM100 was constructed and used in Southern hybridization analysis of strain CS119 and its wild-type parent ATCC 10428 to prove that we had cloned the pagC::TnphoA fusion. The probe contained sequences immediately adjacent to the transposon at the opposite end of the alkaline phosphatase gene (HpaI endonuclease generated DNA fragment that included 186 bases of the right IS50 of the transposon and 1278 bases of *Salmonella* DNA corresponding to the region between 161 and 1439). As expected, the DNA fragment from the strain containing the transposon insertion, CS119, was approximately 7.7 kb (size of TnphoA) larger in size than the fragment from the wild-type strain that hybridizes to the probe. This was consistent with the supposition that we have cloned the pagC::TnphoA fusion. In addition, a derivative of plasmid pSM100, pSM101 (which did not allow expression of the pagC-phoA gene fusion off the lac promoter), was transformed into phoP- (strain CS015) and phoN- (strain CS019) *Salmonella* strains and the cloned AP activity was found to be dependent on phoP for expression. Therefore we concluded that the cloned DNA contained the pagC::TnphoA fusion.

Mapping of Restriction Endonuclease Sites—DNA Sequencing and Determination of the pagC Gene Product Restriction endonuclease analysis of plasmid pSM100 was performed to obtain a physical map of the pagC locus, and to determine the direction of transcription. Appropriate DNA subclones were generated and sequence was obtained from the junctions of the transposon and *Salmonella* DNA. The sequence was also obtained for *Salmonella* DNA extending from the PstI site immediately upstream of the fusion to the EcoRI site downstream of the fusion. The correct reading frame of the DNA sequence was deduced from that required to synthesize an active AP gene fusion. The deduced amino acid sequence contains a methionine start codon 33 amino acids from the fusion of PagC and AP. This 33 amino acid pagC contribution to the fusion protein was consistent with that observed in Western blot analysis and contains a hydrophobic N-terminal region, identified by the method of Kyle and Doolittle ((1892) *J. Mol. Biol.* 157:105–132), that is a typical bacterial signal sequence (Von Heinje (1985) *J. Mol. Biol.* 184:99–105). Specifically, amino acid 2 is a positively charged lysine, followed by a hydrophobic domain and amino acid 24 is a negatively charged aspartate residue. A consensus cleavage site for this leader peptide is predicted to be at an alanine residue at amino acid 23 (yon Heinje (1984) *J. Mol. Biol.* 173:243–251). The DNA sequence also revealed a typical ribosomal binding site at 6–12 nucleotides 5' to the predicted start of translation. This suggested that the open reading frame was, in fact, translated and further supported the assumption that this was the deduced amino acid sequence of the PagC protein interrupted by the TnphoA insertion. The deduced amino acid sequence of the open reading frame was predicted to encode a 188 amino acid protein with a predicted pI=8.2. This was consistent with the 18 kDa protein of pI=8.0, noted to be absent in the 2-D polyacrylamide gel analysis of strain CS119. Therefore identification of the pagC gene product appears established. As documented below, the pagC transcript is approximately 900 nucleotides in length. This is approximately 300 nucleotides greater than that which is devoted to pagC coding sequence, and would seem to preclude the pagC transcript encoding another protein greater than 100 amino acids in size. Therefore, the identified pagC gene product is likely to be the protein essential to virulence and macrophage survival. The pagC gene may be part of a larger operon, but if that is the case, it appears to be the last gene of the operon, and the upstream gene would encode a small protein.

The pagC Gene is Present in Other Strains of *Salmonella*

To test whether other *S. typhimurium* strains LT2, and Q1, as well as *S. typhi* and *S. drypool* contained the pagC gene, chromosomal DNA was prepared from these strains and screened by blot hybridization analysis using a pagC gene probe. All *Salmonella* strains examined demonstrated similar strong hybridization to an 8.0 kb EcoRV-KpnI and a 4.0 kb AccI restriction endonuclease fragment suggesting that pagC is a virulence gene common to *Salmonella* species.

Identification of the pagC Encoded RNA

We purified and analyzed RNA from *S. typhimurium* strains ATCC 10428 (wild-type), CS015 phoP 102::Tn10d-Cam, and C5022 pho-24 (Con) to determine the size of the pagC transcript as well as its dependence on phoP for transcription. An approximately 900 nucleotide RNA is encoded by pagC and this RNA is clearly highly expressed in a strain with a constitutive phenotype of pag activation as compared to wild-type and phoP- bacteria. This suggests, as expected by gene fusion analysis, that pagC is transcriptionally regulated by the phoP gene product and not expressed in early log phase cultures grown in rich media.

Similarity of PagC to Ail and Lom

A computer analysis of protein similarity using the National Biomedical Research Foundation/Protein Identification Resource (George et al., (1986) *Nucl. Acids. Res.* 14:11–15) protein sequence base was conducted to identify other proteins that had similarity to PagC in an attempt to find clues to the molecular function of this protein. Remarkably, PagC was found to be similar to a bacteriophage lambda protein, Lom that has been localized to the outer membrane in minicell analysis (Reeve and Shaw (1979) *Mol. Gen. Genetics* 172:243) as well as demonstrated to be expressed by lambda lysogens of *E. coli*. The deduced amino acid sequence of the cloned ail gene product of *Y. enterocolitica* was determined and found to also be similar to Lom. Therefore, we performed a protein family sequence alignment using a computer algorithm and searched for other members of the family in the data base using a method that has been shown to be more diagnostic for family membership than searching individual sequences (Smith and Smith (1990) *PNAS U.S.A.* 87,118–122). However, no other similarities were found. Regions of similarity are located not only in the leader peptide and transmembrane domains but throughout the protein.

Invasion Phenotype of Wild-Type pagC *Salmonella* Strains

Because of the strong similarity of PagC to ail, PagC- and PhoP- strains were examined in tissue culture models of invasion to assess whether the PagC protein functions as an invasion factor as well as a macrophage survival protein.

TABLE 6

Invasive phenotype of wild-type *S. typhimurium* Strain ATCC 10428 and pagC and phoP mutants*

| Bacterial Strain | HEp-2 | CHO | % Invasion MDCK |
| --- | --- | --- | --- |
| ATCC 10428 (wild-type) | 6.35 | 6.55 | 8.55 |
| CS119 (pagC::Tn phoA | 4.73 | 4.90 | 6.68 |
| CS015 (phoP-) | 1.87 | 2.34 | 4.46 |
| CS022 (phoPconstitutive) | 1.82 | 3.18 | 3.75 |

*Salmonella typhimurium* strains were grown at 28° C. with aeration for 12 to 18 h in LB for the invasion assay. Bacteria (2/10⁷) were added to each well of a 24-well microdilution dish which had been seeded with the indicated tissue culture cells the previous day. The invasion assay was performed as previously described (Miller and Falkow (1988) Infect. Immun. 56:1242-1248) with the exception that the microtiter plates were not centrifuged prior to the first incubation. Values are the averages of duplicate samples, and reflect similar results from several 1.5 experiments.

We were unable to detect more than a modest defect in these strains in these assays. Therefore, we conclude that the PagC protein may not function as an invasion protein, or is not the only pathway by which *Salmonella* invades epithelial cells. This is consistent with the fact that orally administered phoP- *Salmonella* strains pass efficiently from the gut to the liver and spleen.

The above results demonstrate that a number of invasive organisms have one or more common invasive gene(s) which are homologous in a plurality of species. That the gene, inv, as well as a second gene, ail, may be readily transferred to a non-invasive microorganism host to provide for invasion by such microorganism into mammalian cells.

Furthermore, DNA from the genes may be used for an in vitro assay for determining pathogenicity of *Yersinia* species, as well as other species. The invasive genes find further use in identifying strains, evaluating levels of pathogenicity and relationships between pathogenicity and invasion genes.

The mammalian cells are able to endocytose the entire microbial cell based on the presence of a particular structure encoded on the surface membrane of the microorganism. The invasive phenotype can be used for diverse purposes, such as the introduction of exogenous DNA or other molecules into a mammalian host, induction of an immune response to one or a plurality of antigens associated with pathogens, so as to be useful as vaccines, for production of antiserum having a spectrum of antibodies to a spectrum of pathogens, and for the production of proteins which may be used to inhibit invasion of pathogens in mammalian host cells.

EXAMPLE 5

Studies on the Effects of Growth Conditions on the Adherence and Invasiveness of *Salmonella*

Bacterial Strains and Growth Conditions

*Salmonella choleraesuis* strain SL2824 (Nnalue, N. A. and Stocker, B. A. D. (1986) *Infect. Immun.* 54,635–640) and *Salmonella typhi* strain 404Ty were obtained from B. A. D. Stocker (Stanford University School of Medicine, CA). 404Ty is a ΔaroA148 derivative of an Indonesian strain 3083/30 originally characterized by L. LeMinor (Institut Pasteur, Paris, France) which has two flagellar antigen phases, d and z66 (Guinee, P. A. M., Jansen, W. H., Mass, H. M. E., LeMinor, L. and Beaud, R. (1981) *Ann. Microbiol. (Inst. Pasteur)* 132A, 331–334). *Salmonella typhimuirum* strains TN1909 and TN1910, obtained from Charles Miller (Case Western Reserve University, OH), are isogenic strains containing the oxrA+ and oxrA1 loci, respectively. *S. typhimurium* strain LT2 (DB21)) was obtained from David Botstein (Genentech, Calif.). *Salmonella* were grown in LB broth and on LB agar media 9GIBCO, Grand Island, N.Y.), alone or supplemented with 2,3-dihydroxybenzoic acid (DBH) (10 µg/ml) (Sigma, St. Louis, Mo.) which is required for optimal growth of the xaroA mutant strain.

Cultures used in some experiments (Table 7 and Table 8, Expt. III) were grown in LB broth containing antifoam (Sigma Chemical Co., St. Louis, Mo.). The presence of antifoam does not affect the induction or assay of bacterial invasiveness (data not shown). Initially, a culture was grown to logarithmic phase in LB broth containing antifoam while bubbled with air from the laboratory air lines for 2½ hours. This culture was diluted to prepare three cultures which were gently bubbled with different gas mixtures, 5% $CO_2$/ 95% $N_2$, 1% $O_2$/5% $CO_2$/94% $N_2$ or 20% $O_2$/5% $CO_2$/75% $N_2$ (Liquid Carbonic Specialty Gas Corp., San Carlos, Calif.). After 3 hours of additional growth, the final culture density of each culture was ~4×10⁸ CFU/ml (colony-forming units per ml) (Table 7, Expt. I) and ~2×10⁸ CFU/ml (Table 7, Expt. II).

Non-agitated cultures were prepared by inoculation of 2 ml of LB broth in 16×150 mm borosilicate tubes with 0.04 ml of a stationary phase culture. For determining invasiveness, as a percent of inoculum surviving gentamicin, separate cultures were prepared to allow uninterrupted incubation of each sample. It was characteristic of such cultures that, during the initial 3 hour incubation at 37° C., the culture density increased from 10⁸ CFU/ml to 4×10⁸ CFU/ml.

Bacterial growth was much slower during the next 4 hours; the culture density after 7 hours of growth was only $7\times10^8$ CFU/ml. We considered that bacteria from such cultures were in the late logarithmic phase of growth.

Agitated cultures were prepared by inoculation of 1 or 2 ml of LB broth in 16×150 mm borosilicate tubes with a stationary phase culture (a 1:1,000 or 1:50 dilution factor) and placing the tubes on a roller drum (New Brunswick Scientific, Edison, N.J., 80 rpm) at 37° C. Under these growth conditions, logarithmically growing cultures had $\leq 10^9$ CFU/ml. For the experiment concerned with a time course of invasiveness, separate cultures were prepared to allow uninterrupted incubation of each sample.

Overnight cultures were prepared as a source of bacteria in stationary phase by inoculation of 2 ml of broth with $<10^6$ CFU and growth with agitation, except for that used for the experiment determining entry of bacteria *S. choleraesuis* of MDCK cells. In this case, a culture was grown overnight without agitation from a heavy inoculum, as previously described (Finlay, B. B. and Falkow, S. (1988) *Biochimie* 70:1089–1099). Results were similar to those obtained when stationary phase bacteria from an agitated culture were used instead.

Strains were grown at 37° C. with the exception of strains TN1909 and TN1910 which carry a temperature-sensitive Mu dl prophage; they were grown at 30° C. CFU were determined by plating serial dilutions onto LB agar medium.

MDCK cells and growth conditions

Strain 1 MDCK cells (Gumbiner, B. and Simons, K. (1986) *J. Cell Biol.* 102:457–468) were grown in MEM Eagle medium with Earle's salts (Cellgro/Mediatech, Washington, DC), 5% fetal bovine serum (GIBCO, Grand Island, N.Y.), without antibiotics. Monolayers for adherence and invasion assays were prepared by seeding approximately $10^5$ cells into each well of a 24-multiwell tissue culture plate and incubating overnight. MDCK cells between passage 40 and 60 were used for all assays except for those in Table 7 and Table 8 (Expt. III) when cells between passage and 10 were used. The absolute values for bacterial adherence and invasion were ten-fold lower when MDCK cells between passage 8 and 10 were used vs. when those between passage 40 and 60 were used. It is possible that a property of the MDCK cells changed after many serial subcultures resulting in an increased efficiency of bacterial adherence and invasion. The conclusions of this study appear to be unaffected by this potential change in MDCK cells.

Adherence assay

The medium overlying the MDCK monolayers was replaced with 1 ml of ice-cold tissue culture medium and the multi-well dish was placed in an ice-water bath for 30 minutes prior to the assay. Bacterial samples were diluted if necessary in LB broth to approximately $10^8$ to $4\times10^8$ CFU/ml so that addition of 40 μl of each bacterial sample to the MDCK monolayers represented an initial inoculum of $5\times10^6$ to $2\times10^7$ CFU. Control wells without mammalian cells were similarly prepared to quantitate non-specific bacterial adherence to plastic. The bacteria were allowed to adhere on ice for 60 minutes and then each well was rinsed five times with 1–2 ml of ice-cold phosphate-buffered saline (PBS). Adherent bacteria were released by incubation with 0.2 ml 0.1% Triton X-100 (Sigma Chemical Co., St. Louis, Mo.) for 5–10 minutes. 0.8 ml LB broth was then added and each sample was vigorously mixed using a pasteur pipet. Adherent bacteria were quantitated by plating for CFU on LB agar media.

In order to measure internalization of adherent bacteria, bacteria were allowed to adhere as described above. After removal of non-adherent bacteria with the PBS washes, 1 ml of pre-warmed tissue culture medium was added to each assay well and internalization of bacteria was allowed to proceed for 60 minutes at 37° C. in a 5% $CO_2$ incubator. Intracellular bacteria were quantitated after incubation with gentamicin as described below.

Invasion assay

Prior to all invasion assays, the medium overlying each MDCK monolayer was replaced with 1 ml of pre-warmed tissue culture medium. Bacterial samples were then added as described above. Invasion assays were incubated at 37° C. in a % 5 $CO_2$ incubator. Assays were terminated by replacing the overlying medium with 1 ml of tissue culture medium supplemented with 100 μg/ml gentamicin. Gentamicin, an aminoglycoside antibiotic, kills extracellular bacteria while intracellular bacteria remain viable (Vaudaux, P. and Waldvogel, F. A. (1979) *Antimicrob. Agents Chemother.* 16:743–749). After incubation with the gentamicin for 120 minutes at 37° C. in a 5% $CO_2$ incubator, the cell monolayers were washed once with PBS and the viable intracellular bacteria were released by incubation with 0.2 ml 1% Triton X-100 for 5–10 minutes. Samples were vigorously mixed with 0.8 ml LB broth using a pasteur pipet. Viable bacteria were quantitated by planting for CFU on LB agar media.

For the experiment described above, initially tissue culture medium inoculated with $1.4\times10^7$ CFU of *S. choleraesuis* from a stationary phase culture was placed either on MDCK cell monolayers or in empty wells. In the first case, the entry of *Salmonella* into MDCK cells was measured hourly by replacing the overlying medium with tissue culture medium supplemented with 100 μg/ml gentamicin, as described above. In this case, calculations were performed to determine the incremental increase in the number of bacteria that entered the MDCK cells during each one hour period. The invasiveness of the bacteria incubated in tissue culture medium alone was determined by transferring the infected medium onto MDCK cell monolayers at different times. In this case, the number of bacteria that were able to enter the cells during a one hour assay was determined, as described above.

Biosynthetic radiolabelling of *Salmonella* proteins

Bacterial cultures were grown at 37° C. for 5 hours to a final culture density of approximately $10^7$ CFU/ml. Cultures containing tissue culture media were grown in a 5% $CO_2$ incubator. Bacteria from 0.4 ml of each culture were washed with 1 ml of PBS and then resuspended in 80 μl M9 medium (GIBCO Laboratories, Grand Island, N.Y.) containing 0.1% glucose and 15 μCi [$^{35}$S] methionine (Amersham Corp., Arlington Heights, Ill.). Samples were incubated at 37° C. for 1 hour and then centrifuged to harvest the bacteria. The samples were analyzed by sodium dodecyl sulfate polyacrylamide gel electrophoresis (Laemmli, U.K. (1970) *Nature (London)* 227:680–685).

Effect of Growth Conditions on *Salmonella* Invasiveness

Previous work has suggested that *Salmonella* is not inherently able to adhere to or enter mammalian cells (Finlay, B. B., Heffron, F. and Falkow, S. (1989) *Science* 243:940–943). *Salmonella* which were grown to logarithmic phase in LB broth were also found to be inherently non-adherent (Finlay, B. B., Gumbiner, B. and Falkow, S. (1989) *J. Cell Biol.* 107:221–230, Finlay, B. B., Heffron, F. and Falkow, S. (1989) *Science* 243:940–943). Experiments to measure the invasiveness of *Salmonella* that were grown to logarithmic and late logarithmic phase were performed. The results indicate that the invasiveness of bacteria grown under these different conditions varied dramatically. In order to understand this variation, experiments were performed so as to more carefully measure the invasiveness of bacteria during the growth of a culture. Non-agitated and agitated LB broth cultures were examined.

Non-agitated cultures of S. choleraesuis were prepared by inoculation of 2 ml of LB broth with 0.04 ml of a stationary phase culture (a 1:50 dilution factor) at $t_o$. Bacteria grown overnight to stationary phase were not able to enter MDCK cells during a one hour assay. However, after growth of bacteria in non-agitated LB broth for 3 to 7 hours, a 100-fold increase in bacterial invasiveness was observed.

Agitated cultures of S. choleraesuis were prepared by inoculating 2 ml of LB broth with a stationary phase culture (a 1:1,000 or 1:50 dilution factor) at $t_o$. When the ability of bacteria from agitated culture to enter MDCK cells was measured, dramatic differences were seen depending on the stage of growth of the bacteria sample. S. choleraesuis from cultures in logarithmic phase were not maximally invasive. However, when the culture was in late logarithmic phase, bacterial invasiveness increased at least 10-fold. The bacterial culture then lost invasiveness in stationary phase which is consistent with previous observations that bacteria grown overnight in LB broth to stationary phase are non-invasive. Similar results were also found for non-agitated and agitated cultures of S. typhi.

The dramatic differences in the invasiveness of Salmonella from different cultures were not affected by inhibition of bacterial growth and de novo protein synthesis during the assay period. Thus, in the assay performed, the difference in the ability of Salmonella to enter MDCK cells reflects an inherent property of the bacterial inoculum.

Effect of Oxygen Availability of Salmonella Invasiveness

The above experiments show that S. choleraesuis and S. typhi from non-agitated cultures and agitated cultures in late logarithmic phase are at least 10-fold more invasive than those from agitated cultures in logarithmic phase.

A possibly significant difference between these two growth conditions that may account for the differences in Salmonella invasiveness is the availability of oxygen (Strauch, K. L., Lenk, J. B., Gamble, B. L. and Miller C. G. (1985) J. Bacteriol. 161:673–680, Khosla, C. and Bailey, J. E. (1988) Nature 331:633–635).

The amount of oxygen available during bacterial growth was varied by bubbling gas mixtures containing different amounts of oxygen into the culture medium. Unlike the non-agitated and agitated cultures, these bubbled cultures are more easily compared with one another since they can be grown with similar mixing and to similar culture densities. S. choleraesuis and S. typhimurium were grown with gases containing 0% or 1% oxygen were 6- to 70-fold more invasive than those grown with gas containing 20% oxygen (Table 7). These results confirm that Salmonella invasiveness is induced by oxygen-limited growth conditions.

TABLE 7

Effect of Oxygen Availability on
S. choleraesuis and S. typhimurium Invasiveness

| Expt. # | Bacterial species | Bacterial culture* | Bacterial invasiveness (%)[b] |
|---|---|---|---|
| I | S. choleraesuis | non-agitated, late, log | 100 ± 5 |
|   |   | agitated, | 8 ± 0.4 |

TABLE 7-continued

Effect of Oxygen Availability on
S. choleraesuis and S. typhimurium Invasiveness

| Expt. # | Bacterial species | Bacterial culture* | Bacterial invasiveness (%)[b] |
|---|---|---|---|
|   |   | mid-log |   |
|   |   | 0% $O_2$ | 75 ± 0 |
|   |   | 1% $O_2$ | 62 ± 4 |
|   |   | 20% $O_2$ | 13 ± 3 |
| I | S. typhimurium | non-agitated, late log | 100 ± 0 |
|   |   | agitated, mid-log | 0.1 ± 0 |
|   |   | 0% $O_2$ | 41 ± 1 |
|   |   | 1% $O_2$ | 218 ± 18 |
|   |   | 20% $O_2$ | 3 ± 0.3 |

*Bacterial cultures were grown as described previously.
[b]The ability of bacteria to enter into MDCK cells (passage 8 to 10) during one hour was measured as described previously. Assay values represent the average of two separate assays and were normalized such that the invasiveness of bacteria from the non-agitated cultures equals 100%. The actual percent of the inoculum from the non-agitated cultures that entered the MDCK cells was 1.6% and 1.7% for Expts. I and II, respectively.

Invasiveness of a S. typhimurium Mutant Defective in Anaerobic Regulation 33 proteins of S. typhimurium that increase in synthesis in response to anaerobiosis have been detected by two-dimensional gel electrophoresis and subsequently identified (Spector, M. P., Aliabadi, Z., Gonzaler, T. and Foster, J. W. (1986) J. Bacteriol. 168:420–424). The oxrA locus of S. typhimurium is required for the regulation of 14 of these proteins (Strauch, K. L., Lenk, J. B., Gamble, B. L. and Miller, C. G. (1985) J. Bacteriol. 161:673–680, Spector, M. P., Aliabadi, Z., Gonzaler, T. and Foster, J. W. (1986) J. Bacteriol. 168:420–424). The OxrA protein is homologous to the Fnr protein of Escherichia coli which functions as an oxygen-sensitive transcriptional activator during anaerobiosis (Strauch, K. L., Lenk, J. B., Gamble, B. L. and Miller, C. G. (1985) J. Bacteriol. 161:673–680, Sprio, S. and Guest, J. R. (1988) Molec. Microbiol. 2:701–707, Trageser, M. and Unden, G. (1989) Molec. Microbiol. 3:593–599). Since the expression of Salmonella invasiveness is induced in oxygen-limited growth conditions, the invasiveness of isogenic oxrA+/oxrA− S. typhimurium strains grown in aerobic and oxygen-limited conditions was examined. The oxrA+ and oxrA− strains were shown not to differ in their ability to enter MDCK cells. Both strains exhibited a 100-fold increase in invasiveness when grown in oxygen-limited vs. aerobic conditions. Thus, the oxrA locus does not regulate the expression of Salmonella invasiveness.

Adherence and Entry of Salmonella choleraesuis to MDCK Cells

It has been proposed that Salmonella initially bind to the mammalian cell surface and are subsequently internalized by a host-direct endocytic/phagocytic process (Finlay, B. B. and Falkow, S. (1988) Biochimie 70:1089–1099, Moulder, J. W. (1985) Microbiol. Rev. 49:298–337). Thus, alteration of either the binding properties or the efficiency of the internalization process would affect bacterial invasiveness. S. choleraesuis grown in different cultures conditions were examined for changes in their ability to bind to, and subsequently enter MDCK cells. A similar assay for adherence and internalization has been used to examine the interaction between the Yersinia pseudotuberculosis invasion protein and its mammalian receptor (Isberg, R. R. (1989) Molec. Microbiol. 3:1449–1453, Isberg, R. R., Voorhis, D. L. and Falkow, S. (1987) Cell 50:769–778).

Although *S. choleraesuis* does not bind efficiently to MDCK cells in this assay, the data in Table 8 revealed that bacteria from oxygen-limited cultures were able to adhere to MDCK cells 20- to 100-fold better than bacteria from aerobic cultures. Bacteria from stationary phase also appeared to adhere to MDCK cells. Measurement of the number of adherent bacteria that were able to subsequently enter the MDCK cells demonstrated that a relatively high percentage of bacteria were internalized in all cases, except for the bacteria from stationary phase. Adherent stationary phase bacteria were internalized 100-fold less efficiently, a finding consistent with previous observations that such bacteria are not invasive.

TABLE 8

Adherence and Subsequent Internalization of *S. choleraesuis* into MDCK Cells

| Expt. #[a] | Bacterial culture[b] | Bacterial adherence at 0° C. (%)[c] | Internalization of adherent bacteria at 37° C. (%)* |
|---|---|---|---|
| I | non-agitated, late log | 100 ± 15 | 59 ± 7 |
|   | agitated, late log | 26 ± 1 | 35 ± 2 |
|   | agitated, mid-log | 0.8 ± 0.5 | 54 ± 11 |
|   | stationary phase | 22 ± 2 | 0.3 ± 0.1 |
| II | non-agitated, late log | 100 ± 8 | 40 ± 5 |
|   | agitated, late log | 40 ± 0.5 | 16 ± 9 |
|   | agitated, mid-log | 6 ± 0.4 | 15 ± 6 |
|   | stationary phase | 83 ± 16 | 0.4 ± 0.1 |
| III | non-agitated, late log | 100 ± 16 | 7 ± 0.1 |
|   | agitated, late log | 83 ± 8 | 7 ± 2 |
|   | agitated, mid-log | 58 ± 7 | 9 ± 0.3 |
|   | stationary phase | 2 ± 1 | —** |

[a]MDCK cells between passage 40 and 60 were used for Expt. I and II whereas those between passage 8 and 10 were used for Expt. III.
[b]Bacterial cultures were prepared as described above.
[c]Assay values represent the average of two separate assays and were normalized such that the adherence of bacteria from the non-agitated cultures equals 100%. The actual percent of the inoculum from the non-agitated cultures that were adherent was 1.6%, 1.2% and 0.12% for Expts. I, II and III, respectively.
*Values represent the average of two separate assays.
**Values were too low to allow calculation.

Induction of *S. choleraesuis* Invasiveness in the Presence and Absence of MDCK Cells Previous experiments have shown that *S. choleraesuis* grown overnight in LB broth is not inherently able to enter MDCK cells. However, after further incubation with the mammalian cells in tissue culture medium, bacteria adherence and invasiveness was induced. It has been proposed that induction of invasiveness might occur in response to exposure to the epithelial cell surface (Finlay, B. B., Heffron, F. and Falkow, S. (1989) *Science* 243:940–943). The induction of invasiveness seen in the experiment in Table 8 may have been due to the presence of the MDCK cells, or to a change in bacterial growth state during the incubation period. Experiments to distinguish between these two possibilities were performed by comparing the invasiveness of *S. choleraesuis* incubated with MDCK cells vs. *S. choleraesuis* incubated identically in tissue culture medium but in the absence of MDCK cells. The results obtained revealed that regardless of the presence of MDCK cells, bacterial invasiveness was induced 40-fold after four hours of incubation. Thus in this in vitro system, induction of *Salmonella* invasiveness can be accounted for by growth in tissue culture medium alone.

Analysis of Proteins Synthesized by Invasive *Salmonella*

In order to identify the major proteins expressed by invasive *Salmonella*, *S. choleraesuis* and *S. typhi* grown under different culture conditions were radiolabelled. Invasive bacteria from non-agitated cultures were compared with bacteria from agitated culture (which are at least 10-fold less invasive than the bacteria grown in the non-agitated). Proteins with approximate molecular weights of 65 Kd and 44 Kd were found to be preferentially produced by invasive *Salmonella*. By comparison to previously published protein patterns, it appears that both of these proteins have been identified as expressed by *Salmonella* adherent to MDCK cells (Finlay, B. B., Heffron, F. and Falkow, S. (1989) *Science* 243:940–943).

EXAMPLE 6

The following describes the identification of the inv gene analog in *H. influenzae*.

Bacterial Strains and Culture Conditions

*H. influenzae* strain SU1 is a clinical isolate which was obtained from the Clinical Microbiology Laboratory at Stanford University Hospital. It is nonencapsulated and appears to be a nontypable strain on the basis of multilocus enzyme electrophoresis. Negative staining electron microscopy demonstrates that this strain is nonpiliated. It was stored frozen at −80° C. in brain heart infusion broth with 20% glycerol. For all assays bacteria were streaked from frozen aliquots onto fresh chocolate agar supplemented with 1% Supplement VX (Difco Laboratories, Detroit, Mich.) and were grown at 37° C. in a 5% $CO_2$ incubator overnight. For growth in broth, bacteria were suspended from an 18 hour chocolate agar plate in brain heart infusion broth supplemented with hemin (10 µg/ml) and NAD (3.5 µg/ml).

*Escherichia coli* K12 was obtained from the Stanford University collection and is the Stanford wild-type prototrophic strain (ATCC 10798). It was stored frozen at −80° C. in LB broth with 50% glycerol and was grown either on LB agar plates or in LB broth (GIBCO, Grand Island, N.Y.).

Tissue Culture Cells

Chang epithelial cells, Wong-Kilbourne derivative, clone 1-5c-4 (human conjunctiva) were obtained from the American Type Culture Collection (ATCC CCL20.2). Cells were maintained in Modified Eagles Medium with Earle's salts and nonessential amino acids (Irvine Scientific) supplemented with 10% heat-inactivated fetal calf serum (GIBCO, Grand Island, N.Y.) and 2.0 mM 1-glutamine. They were subcultivated every two to five days and were used between passages three and fifty. For adherence and invasion assays, approximately $1.5 \times 10^5$ cells suspended in 0.5 ml of tissue culture medium were seeded into each well of 24-well tissue culture plates (Becton Dickinson Labware) which were then incubated at 37° C. in 5% $CO_2$ for 18 to 20 hours. In the case of radiolabeled adherence assays, cells were seeded onto 12 mm diameter glass coverslips placed on the bottom of each well of tissue culture plates.

Adherence Assays (i) Radiolabeled assay

Bacteria were suspended in supplemented brain heart infusion broth and grown at 37° C. with aeration to late log phase ($10^9$ CFU/ml). They were pelleted, washed once with phosphate buffered saline (PBS), pH 7.0, and resuspended in methionine assay medium (Difco Laboratories, Detroit, Mich.). After incubation at 37° C. with aeration for 15 minutes, 50 µCi of [$35_{S]methionine}$ (Amersham, Arlington Heights, Ill.) was added to the suspension along with hemin and NAD and incubation was continued for another 45 minutes. While there was minimal bacterial growth during the period of radiolabeling, on average the level of incorporation of radioactivity was 0.01 cpm/bacterium. Radiolabeled bacteria were washed three times with PBS, resuspended in PBS, and inoculated (10 µl, $1-2\times10^7$ CFU) onto monolayers. Tissue culture plates were incubated at 37° C. (5% $CO_2$) for various times. After the desired incubation period, the infected monolayers were rinsed three times with PBS with gentle rocking to remove nonadherent bacteria. Nonspecific adherence was determined by inoculating radiolabeled bacteria onto coverslips without epithelial cells, followed by rinsing with PBS. Coverslips were transferred to vials containing 5 ml of aqueous counting scintillant (ACS II; Amersham, Arlington Heights, Ill.) and counts were determined and compared with the inoculum. Expression of adherence as percent of original radioactivity provides a measure of bacterial attachment which is independent of later bacterial events, such as replication. Calculations of the average number of adherent bacteria per eukaryotic cell accounted for bacterial replication and assumed no epithelial cell division during the course of an assay.

(ii) Viable Count Assay

Bacteria were grown to log phase as for the radiolabeled adherence assay. Approximately $1-2\times10^7$ CFU (10 µl) were inoculated directly from the broth culture onto monolayers, and tissue culture plates were incubated at 37° C. in 5% $CO_2$. Following the appropriate incubation period, monolayers were rinsed four times with PBS and then treated with trypsin-EDTA (0.05% trypsin, 0.5 mM EDTA) in PBS to release them from the plastic support. Well contents were agitated, and dilutions were plated on supplemented chocolate agar for *H. influenzae* or LB agar for *E. coli*, yielding the number of adherent bacteria per monolayer.

Invasion Assay

To determine the number of bacteria entering the cells of an epithelial monolayer we adapted the assay of Isberg and Falkow (*Nature* (1985) 317:262–64) Briefly, bacteria were grown and monolayers were infected as outlined above for the viable count adherence assay. After the desired incubation, monolayers were rinsed three times with PBS, and fresh tissue culture medium containing gentamicin (100 µg/ml) was added. Tissue culture plates were incubated for another two hours, rinsed twice with PBS, then treated with trypsin-EDTA (0.05% trypsin, 0.05 mM EDTA) in PBS. Well contents were agitated and dilutions were plated to quantitate the number of internalized bacteria per monolayer.

Outer Membrane Protein Analysis

Outer membrane fractions were prepared from samples of radiolabeled bacteria using the microprocedure of Carlone et al. with minor modifications. (*J. Clin. Microbiol.* (1986) 24:330–32). Bacteria were initially pelleted by centrifugation a 5000×g and 4° C. for 10 minutes. Pellets were washed once with 1 ml of cold 10 mM HEPES (N-2-hydroxyethylpiperazine-N'-2-ethanesulfonic acid) buffer, pH 7.4, then resuspended in 1 ml of the same buffer in preparation for sonication. Samples were sonicated on ice with eight 10 second bursts at maximal output using a microsonicator and a 2.3 millimeter probe (Kontes). Intact cells were removed by centrifugation at 15,600×g and 4° C. for 2 minutes in a microcentrifuge (Brinkmann). Supernatants were decanted into fresh tubes and centrifuged at 15,600×g and 4° C. for 30 minutes to pellet bacterial membranes. Pellets were resuspended in 0.2 ml 10 mM HEPES buffer (pH 7.4). Following the addition of 0.2 ml of 2% sarcosyl (N-lauroyl sarcosine) in 10 mM HEPES buffer (pH 7.4) to solubilize cytoplasmic membranes, samples were incubated at room temperature for 30 minutes with intermittent mixing. Insoluble fractions containing outer membranes were collected by centrifugation at 15,600×g and 4° C. for 30 minutes. The outer membranes were resuspended in equal quantities of distilled water and Laemmli buffer (Laemmli, *Nature* (1970) 227:680–685) and were stored at −20° C. Samples were heated at 100° C. for 5 minutes, and 100,000 cpm were loaded onto sodium dodecyl sulfate-polyacrylamide gels. Electrophoresis was performed at a constant current of 25 mA with stacking and resolving gels which contained 5% and 10% polyacrylamide, respectively. Gels were stained with Coomassie blue for 30 minutes and were destained overnight. Autoradiograms were made using XAR-5 film.

Microscopy (i) Transmission Electron Microscopy

Chang epithelial cells were seeded into 35 mm×10 mm Contur Permanox tissue culture dishes (Miles Scientific, Naperville, Ill.) and bacteria were inoculated onto monolayers as above. Following the appropriate incubation period, monolayers were rinsed four times with PBS and fixed with 2% glutaraldehyde in 0.1M sodium phosphate buffer, pH 7.4 at 4° C. for 2 hours. After washing with 0.1M sodium phosphate buffer, samples were postfixed with 1% OsO4 in sodium phosphate buffer for 90 minutes and then incubated in buffer overnight. Samples were next washed with distilled water and stained with 0.25% aqueous uranyl acetate for 1 hour. They were dehydrated with a series of graded ethanol solutions and embedded in a firm Spurr resin. Samples were sectioned, stained with uranyl acetate and lead citrate, and examined in a Phillips 201c electron microscope.

(ii) Scanning electron microscopy

Monolayers were prepared on glass coverslips as for radiolabeled adherence assays. They were inoculated with bacteria and incubated for variable periods of time, followed by rinsing four times with PBS. Samples were fixed with 2% glutaraldehyde in 0.1M sodium phosphate buffer, pH 7.4 for two hours, then dehydrated in a critical point apparatus (Polaron). After a gold evaporation step, samples were examined with a JEOL scanning electron microscope.

(iii) Light Microscopy

Monolayers were prepared on glass coverslips as above. After inoculation of bacteria and incubation for the desired period of time, monolayers were rinsed four times with PBS. Samples were fixed with HPLC grade Methanol for 15 minutes and were then stained with Giemsa stain diluted 1:20 for 30 minutes. They were rinsed four times with distilled water and were mounted on glass slides for viewing by light microscopy.

Adherence

Using radiolabeled bacteria and measuring adherence as percent of original radioactivity, we noted minimal adherence by strain SU1 after one hour of incubation with the epithelial monolayer. However, adherence continued to increase over time, peaking about ten-fold higher by four to six hour. In contrast, there was minimal nonspecific adherence with no significant change over time. *E. coli* K12 demonstrated negligible adherence which failed to change appreciably over the course of an assay. Adherence by *E. coli* was measured up to four hours; at later time points the monolayer began to lose integrity. Adherence by *H. influenzae* strain SU1 gradually increased from 0.5% at one hour to greater than 8% by six hours. Because of bacterial replication that occurred during the course of the assay, the actual number of adherent bacteria per eukaryotic cell increased more than 100-fold between hours one and six. The kinetics of adherence appeared similar for inocula varying between $10^6$ and $10^8$ CFU. Examination of Giemsa stained samples and results from the viable count adherence assay confirmed this gradual increase in adherence over time with a peak at four to six hours.

This increment in adherence with time suggested a dynamic interaction between infecting *H. influenzae* and the epithelial monolayer. To begin to explore the nature of this interaction, we examined adherence to a monolayer which had been chemically fixed for two hours with 2% glutaraldehyde. Fixation virtually abolished bacterial attachment, implying the importance of viable epithelial cells or a receptor cross-linked by glutaraldehyde or both. In contrast, treatment of monolayers with emetine dihydrochloride (Streeter and Rees, *J. Cell. Biol.* (1987) 105:507–15), a selective inhibitor of eukaryotic protein synthesis, had no effect on adherence. In initial studies of bacterial events occurring during the course of the bacteria-epithelial cell interaction, we pretreated bacteria with the bactericidal antibiotic gentamicin and then added these nonviable bacteria to the cell monolayer. Adherence by nonviable bacteria was markedly reduced compared with viable organisms. By six hours there were an average of two bacteria per eukaryotic cell. Incubation at 4° C. produced a similar inhibition of adherence. Addition of a bacteriostatic concentration of tetracycline (6 µg/ml) to the monolayers just prior to inoculation of viable bacteria again produced a marked inhibition of adherence, indicating the need for protein synthesis at some point following initial exposure to the epithelial cell monolayer. To extend this observation, we introduced tetracycline following incubation for one hour and two hours and then measured adherence at six hours in each case. In the presence of tetracycline there was minimal further adherence from hour one to six and hour two to six, respectively, implying a need for ongoing protein synthesis throughout the period of incubation in order for maximal adherence to occur. Examination by light microscopy confirmed the results.

The above evidence demonstrating a requirement for ongoing protein synthesis suggested that an adhesin might be induced during the incubation. Bacteria sampled at one, two, four, and six hours were unable to agglutinate human erythrocytes, arguing against pili as the putative adhesin. Similarly, negative staining electron microscopy on bacteria examined after incubation for six hours revealed no pili-like structures.

Identification of Candidate Adhesin Molecules

To identify candidate proteins which might be mediating the process of adherence, we compared profiles of outer membrane proteins synthesized during incubation with epithelial cells for adherent versus nonadherent populations of bacteria. In this experiment, methionine free Dulbecco's MEM was substituted for the usual tissue culture medium and emetine dihydrochloride was added to monolayers to inhibit selectively eukaryotic cell protein synthesis. Bacteria were then inoculated onto monolayers and were radiolabeled with [$^{35}$S]methionine from hours two to four of incubation. Following the period of radiolabeling, we separated bacteria remaining in the supernatant (nonadherent) from those associated with the epithelial monolayer (adherent). As a control we simultaneously radiolabeled bacteria incubated in tissue culture media alone (i.e., in the absence of a monolayer). Subsequently we isolated detergent-insoluble proteins from adherent bacteria, supernatant bacteria, and bacteria labeled in media alone. To confirm that emetine had completely inhibited protein synthesis by the epithelial monolayer, we performed the same procedure on an uninfected monolayer radiolabeled for two hours. This analysis yielded several notable results. Specifically, adherent bacteria expressed at least three protein bands which were absent from either supernatant or control bacteria (molecular weights approximately 16, 20, and 80 kilodaltons). In addition, there were at least five other protein bands which were expressed more prominently by adherent bacteria (36, 44, 46, 56, and 72 kilodaltons). Expression of a protein of molecular weight 28 kilodaltons was diminished in adherent organisms compared to supernatant or control bacteria. Western analysis using an antiserum directed against a 13-amino acid peptide of *H. influenzae* type b pilin (Rabbit antiserum R 13, provided by J. Gilsdorf, Univ. of Michigan School of Medicine) demonstrated no reactivity with any of these proteins. This antiserum recognizes pilins from all of the type b and nontypable *H. influenzae* strains tested (Gilsdorf et al. *Pediatr. Res.*, (1990) 27:170A).

Invasion

Bacterial invasion was determined on the basis of the ability to survive treatment with gentamicin. Gentamicin is a bactericidal antibiotic which is unable to enter eukaryotic cells. Therefore, bacteria adherent to epithelial cells are killed by this drug while internalized organisms are protected from its effects (Kihlstrom and Andaker, *J. Antimicro Chemo.* (1985) 15:723–728). Preliminary experiments indicated that a concentration of gentamicin equal to 100 µg/ml was sufficient to kill 100% of an inoculum of $5 \times 10^8$ bacteria for strain SU1.

Using this assay, strain SU1 showed increasing numbers of internalized bacteria per monolayer over time, rising from $2 \times 10^1$ at one hour to nearly $10^5$ at five and one half hours. Thus, by this later time point there was on average approximately one intracellular organism per epithelial cell in the monolayer. Correcting for bacterial replication by calculating the ratio of internalized bacteria to total bacteria present at each time point confirmed an increase with time in the ability of bacteria to enter. In contrast, invasion by bacteria which were incubated in the presence of tetracycline was nearly completely inhibited. *E. coli* K12, a noninvasive organism, showed virtually no invasion in this assay. Invasion by *E. coli* was measured up to four hours; as noted above, at later time points the monolayer began to lose integrity.

As most invasive bacteria enter eukaryotic cells via a microfilament-dependent process (Moulder, *Microbiol. Rev.* (1985) 49:298–337), we examined the effect of cytochalasin D on the process of invasion by *H. influenzae*. Cytochalasin D is a potent inhibitor of microfilament formation which at a concentration of 1 µg/ml prevents entry of a variety of cell lines by a number of different bacterial species. Using this concentration of cytochalasin D and an incubation time of four hours, we noted a marked reduction in the number of internalized bacteria for strain SU1. Interestingly, inhibition of microtubules with concentrations of colchicine ranging from 0.5 to 5 µg/ml also resulted in a profound decrease in invasion. There was no effect on adherence by either cytochalasin D or colchicine.

Microscopy

We used scanning and thin section transmission electron microscopy to confirm our results with the aforementioned adherence and invasion assays and to gain additional information about the interaction between infecting *H. influenzae* and Chang conjunctival cells. The general sequence of events was viewed with scanning microscopy. At one hour there were occasional cells with a few associated bacteria. In each case it was apparent that initial contact between bacteria and the cell surface occurred via attachment to microvilli. Most cells were free of adherent bacteria at this early time point and were morphologically identical to uninfected monolayers. By two hours a majority of cells had adherent bacteria, and the number of bacteria per cell was greatly increased compared with one hour. By four hours there was a further increase in the number of epithelial cells with associated bacteria and a peak in the number of bacteria per cell. The six hour samples revealed a slight decrement in adherence and early evidence of a toxic effect on the epithelium with beginning loss of microvilli. Higher magnification (20,000 to 30,000×) demonstrated no obvious bacterial surface appendages at either early or late time points.

Transmission electron microscopy also demonstrated that initial contact with the epithelium involved interaction with microvilli. Subsequently, bacteria moved into direct contact with the plasma membrane of host cells and occasionally were seen penetrating this surface. By two to four hours there were obvious internalized organisms. In general, in a given thin section invaded cells had one or a few internalized bacteria, and sometimes bacteria were seen in pairs. It was difficult to resolve definitively whether internalized bacteria were enclosed by a vacuole, although occasionally they appeared to be. At six hours there were numerous cells with one to several internalized bacteria.

EXAMPLE 7

The following describes the identification of the hil gene in *Salmonella typhimurium* utilizing a novel approach based on the finding that *Salmonella* invasiveness is regulated by oxygen.

Bacteria grown aerobically are less invasive than bacteria grown under oxygen-limiting conditions (Lee, C. A. and Falkow, S. (1990) *Proc. Natl. Acad. Sci. U.S.A.* 87:4304–4308; Ernst, R. K., Dombroski, D. M. and Merrick, J. M. (1990) *Infect. Immun.* 58:2014–2016, and Schiemann, D. A. and Shope, S. R. (1991) *Infect. Immun.* 59:437–440). It was reasoned that mutants which constitutively express *Salmonella* invasion factors might enter epithelial cells even when grown aerobically. The following describes the identification and characterization of such hyper-invasive *S. typhimurium* mutants.

In order to identify *S. typhimurium* genes involved in epithelial cell entry, mutants were selected that entered HEp-2 cells when grown under repressing, aerobic culture conditions. Two types of transposons were used to generate bacterial mutations, transposons that disrupt genes (Tn10 and Tn5) and one transposon (Tn5B50) that, in addition to disrupting genes, can cause constitutive expression of genes from the neo promoter at one end of the transposon. Three classes of mutations were found which increased the ability of aerobically grown *S. typhimurium* to enter HEp-2 cells. One class of mutations disrupt the che operons and result in a non-chemotactic phenotype. The second class of mutations revealed that defects in rho, which encodes an essential transcription termination factor, result in hyper-invasiveness. The third class of mutations was obtained from mutagenesis with Tn5B50, suggesting that their increased invasiveness is due to constitutive expression of a gene(s) from the exogenous neo promoter. Analysis of this third class of mutations identified a *S. typhimurium* locus hil (hyper-invasion locus) which is essential for bacterial entry into epithelial cells. The results suggest that hil encodes an invasion factor or an activator of invasion factor expression. hil maps between srl and mutS near minute 59.5 of the *S. typhimurium* chromosome, a region adjacent to other loci that have been identified as required for *S. typhimurium* invasiveness and virulence.

Genetic and Molecular Biological Techniques

P22-mediated transduction was conducted as previously described (Davis, R. W., Botstein, D. and Roth, J. R. (1980) in Advanced Bacterial Genetics: A manual for genetic engineering (Cold Spring Harbor Laboratory, Cold Spring Harbor, N.Y.)). Isogenic rho$^{ts}$-111 and rho$^+$ strains were constructed by transduction of ilv::Tn10 from AA965 (Housley, P. R., Leavitt, A. D. and Whitfield, H. J. (1981) *J. Bacteriol.* 147:13–24) to SL1344 (Hoiseth, S. K. and Stocker, B. A. (1981) *Nature* 291:238–239) and screening for acquisition of temperature-sensitivity (rho$^{ts}$-111) or maintenance of temperature-resistance (rho$^+$). Tn5 insertions linked to Tn5B50-380 were isolated by P22-mediated transduction of Tn5 from pools of random EE251::Tn5 strains (see below) to SL1344::Tn5B50-380. Kanamycin-resistant transductants were replica-plated onto media containing kanamycin and tetracycline to identify those desired transductants that had consequently lost the Tn5B50 mutation.

DNA from P22 phage particles was isolated from mitomycin C-induced phage lysates of 70 Mud-P22 strains (N. Benson and B. Goldman, unpublished results; Gillen, K. L. and Hughes, K. T. (1991) *J. Bacteriol.* 173:2301–2310) by precipitation of phage with 3% polyethylene glycol (MW–8000) and 0.375M sodium chloride. Phage were resuspended in dilution buffer (Davis, R. W., Botstein, D. and Roth, J. R. (1980) in Advanced Bacterial Genetics: A manual for genetic engineering (Cold Spring Harbor Laboratory, Cold Spring Harbor, N.Y.)) before serial extraction with chloroform and phenol. Phage particle DNA was recovered by precipitation from the aqueous phase with ethanol in the presence of 0.3M sodium acetate.

*S. typhimurium* DNA flanking Tn5 or Tn5B50 mutations was cloned by selection of chromosomal DNA fragments containing the antibiotic-resistance gene of the transposon. The restriction pattern of the genetic locus associated with hyper-invasion was deduced by restriction analysis of these DNA fragments as well as their use in Southern analysis of *S. typhimurium* chromosomal DNA. Collectively, four DNA fragments contain the 20 kb of *S. typhimurium* chromosomal DNA depicted in FIG. 1, except for 2.6 kb at the extreme left end and 2 kb downstream of the third BamHI site. DNA probes were labelled with $^{32}$P-dCTP by nick-translation and DNA-DNA hybridization was conducted on nitrocellulose filters as previously described (Maniatis, T., Fritsch, E. F. and Sambrook, J. (1982) in Molecular Cloning: A laboratory manual (Cold Spring Harbor Laboratory, Cold Spring Harbor, N.Y.)).

DNA flanking Tn5-317 was cloned by selection for a BamHI chromosomal DNA fragment from EE251::Tn5-317 containing the kanamycin-resistance gene of Tn5. The sequence of *S. typhimurium* DNA flanking the Tn5 was determined by a chain-termination sequencing method (U.S. Biochemical, Sequenase 2.0, Cleveland, Ohio) using a primer complementary to the end of IS50.

Bacterial and tissue culture growth conditions

Bacterial strains were grown in LB broth (Luria-Bertani; 1% Bacto-tryptone (Difco), 0.5% Bacto-yeast extract (Difco), 0.8% sodium chloride) or on LB agar (GIBCO). Media were supplemented with antibiotics when necessary; 100 μg/ml ampicillin, 25 μg/ml kanamycin, 100 μ/ml streptomycin and/or 10 μ/ml tetracycline. Strains were grown at 37° C., except that those used to examine the effect of rhot$^{ts}$-111 were grown at 30° C. Two different growth conditions were used to assess the effect of oxygen limitation on S. typhimurium invasiveness. Aerobic cultures were prepared by first growing bacteria to stationary phase. Stationary phase cultures were prepared by inoculating 2 ml of LB broth in 16×150 mm borosilicate tubes with bacteria from a colony. After rolling the tubes on a rotator drum for approximately 20 hours, the bacteria were in stationary phase for at least 12 hours. Approximately 10$^6$ colony forming units (cfu) from such stationary phase cultures were then inoculated into 1 ml of LB broth in tubes. Aerobic cultures with a final density of ~10$^4$ cfu/ml were obtained after placing the tubes on a rolling rotator drum for 2 to 3 hours. Oxygen-limited cultures were prepared by inoculation of 5 ml of LB broth in 16×150 mm tubes with ~10$^4$ cfu/ml. The tubes were incubated without agitation overnight until the cultures reached a density of 5×10$^8$ to 10 cfu/ml.

HEp-2 cells (ATCC CCL23), a line established from a human epidermoid carcinoma, were grown without antibiotics in RPMI 1640 medium (Whittaker, Walkerville, Md.) supplemented with 5% fetal bovine serum (GIBCO). Monolayers for bacterial invasion were prepared by seeding ~10$^5$ cells into each well of a 24-multiwell tissue culture plate and incubating overnight at 37° C. in 5% CO$_2$.

Transposon mutagenesis of Salmonella typhimurium

S. typhimurium strain SL1344 was mutagenized with Tn10 using a phage lysate from DB5204 (Davis, R. W., Botstein, D. and Roth, J. R. (1980) in Advanced Bacterial Genetics: A manual for genetic engineering (Cold Spring Harbor Laboratory, Cold Spring Harbor, N.Y.)). Tails were added to the defective P22 phage particles by incubation with extracts from E. coli 294/pPB13 (Sauer, R. T., Krovatin, W., Poteete, A. R. and Berget, P. B. (1982) Biochemistry 21:5811–5815). Two SL1344::Tn10 pools were generated, each containing 1,000 to 5,000 independent transposon mutants.

S. typhimurium strain EE251, a spontaneous streptomycin resistant derivative of SL4012 (Collins, A. L. and Stocker, B. A. (1976) J. Bacteriol. 128:754–765) was mutagenized with Tn5 or with Tn5B50 using a delivery system based on plasmid pRTP1 (Stibitz, S., Black, W. and Falkow, S. (1986) Gene 50:133–140). Initially, each transposon was moved by transposition from lambda derivatives (Simon, R., Quandt, J. and Klipp, W. (1989) Gene 80:161–169) to pRTP1 in the non-suppressing E. coli host strain MC4100. pRTPi::Tn5 and pRTPl::Tn5B50 were selected such that the transposon insertion did not disrupt the bla or rpsL genes on the plasmid. The mutagenesis system is based on the fact that strain EE251 contains a streptomycin-resistant allele of rpsL which is phenotypically recessive to the streptomycin-sensitive rpsL allele on the pRTP1 derivatives. In this way, transposition of Tn5 or Tn5B50 onto the genome of strain EE251 and subsequent loss of the plasmid can be selected for by growth of such EE251::Tn mutants in the presence of streptomycin and kanamycin (for Tn5; or tetracycline for Tn5B50).

For example, to generate one pool of EE251::Tn5 mutants, an exponentially growing culture, derived from a single colony of EE251/pRTPl::Tn5, was diluted and 5,000 to 10,000 cfu were plated onto L agar containing kanamycin. The plate was incubated overnight at 30° C. to allow growth of the colonies. In order to select for the EE251::Tn5 mutants within each colony, the colonies were replica plated onto L agar containing streptomycin and kanamycin. The replica plate was incubated overnight at 37° C. and the streptomycin resistant, kanamycin-resistant colonies were scraped from the agar and pooled. The replica plating procedure also serves to reduce the effect of unequal representation of transposon mutations that occurred at different times during growth at 30° C. since each independent mutant can only grow to the size of a colony on the selection medium. Using this procedure, almost every original kanamycin-resistant colony gave rise to an independent streptomycin-resistant, kanamycin-resistant colony on the replica plate. The surprisingly efficient selection of these transposon mutants that have lost the dominant streptomycin-sensitive pRTP1 derivative is likely due to the random segregation properties of the colE1 plasmid (Ayala, S. J. and Gomez, E. M. (1989) Mol. Microbiol. 3:1745–1752). Approximately 0.2% of the cfu in each pool remained ampicillin-resistant and likely were streptomycin-resistant due to mutation of the rpsL gene on the pRTP1 derivative. Ten to 12 independent pools of EE251::Tn5 and EE251::Tn5B50 mutants were generated by this procedure.

Selection for hyper-invasive S. typhimurium mutants

The selection procedure is based on the fact that extracellular bacteria are killed by gentamicin whereas intracellular bacteria are protected from exposure to the antibiotic (Vaudaux, P. and Waldvogel, F. A. (1979) Antimicrob. Agents Chemother. 16:743–749). To enrich for mutants that can enter HEp-2 cells even when grown aerobically, two different aerobic cultures were grown from each independent pool of S. typhimurium transposon mutants. One-tenth of a ml of each culture was then inoculated into the medium overlying HEp-2 monolayers. Bacteria were allowed to enter the HEp-2 cells during a one hour incubation at 37° C. in 5% CO$_2$. The medium was then changed to RPMI 1640 containing 5% fetal bovine serum and 100 μ/ml gentamicin, so that the extracellular bacteria were preferentially killed during an additional two hour incubation. To release any intracellular bacteria, the monolayers were rinsed twice with phosphate-buffered saline (PBS) and incubated with 50 μl 1% Triton X-100 for 10 minutes at room temperature. The viable bacteria were recovered as a saturated bacterial culture by adding 1 ml of LB broth to each well and agitating the entire dish overnight. The next day, the saturated culture was used to prepare an aerobic culture and the enrichment procedure was repeated. After four sequential enrichment cycles, intracellular bacteria were released from the HEp-2 cells and directly plated onto LB agar. Enumeration of the cfu released from each monolayer indicated which wells contained mutant strains that were more invasive than the wild-type S. typhimurium. Single colonies from such wells were purified and analyzed.

Mutant analysis

S. typhimurium transposon mutants obtained from the selection procedure were (1) assayed for their ability to enter HEp-2 cells (see below), (2) reconstructed into both SL1344 and EE251 strain backgrounds, crossing out the transposon mutation by P22-mediated transduction and (3) re-tested after reconstruction for invasiveness. From this analysis, independent transposon mutations which were found to result in at least a 10-fold increase in aerobic invasiveness were saved and analyzed further.

Bacterial invasiveness was assayed by inoculating ~10$^7$ cfu into the medium overlying a HEp-2 monolayer. Bacteria were allowed to enter the HEp-2 cells during a one hour incubation. After a two hour treatment with gentamicin, the cell monolayer was rinsed with PBS and disrupted by incubation with 0.2 ml 1% Triton X-100. Each sample was vigorously mixed with 0.8 ml LB broth using a pasteur pipet and the viable bacteria were quantitated by plating for cfu on LB agar. Differences in bacterial invasiveness were verified by Giemsa staining of infected monolayers and direct microscopic observation of bacterial association with cells.

Identification and Characterization of Hyper-Invasive S. typhimurium Mutants

Tn10, Tn5 and Tn5B50 mutants of S. typhimurium were selected by their ability to enter epithelial cells after aerobic growth. Positive selection of such mutants by their ability to resist killing by gentamicin in infected HEp-2 cells allowed their identification from large pools of random mutants. Sixteen independent transposon mutations, three Tn/10, five Tn5 and eight Tn5B50 insertions, were found to increase the ability of aerobically grown S. typhimurium to enter HEp-2 cells by 13- to 74-fold (Table 9).

TABLE 9

Effect of representative transposon mutations on S. typhimurium SL1344 invasiveness

| SL1344 derivative | Relative Invasiveness* | |
|---|---|---|
| | aerobic growth condition | low oxygen growth condition |
| wild-type | 1 ± 0.2 | 43 ± 2 |
| ::Tn10-181 | 13 ± 4 | 54 ± 10 |
| ::Tn10-177 | 16 ± 5 | 62 ± 8 |
| ::Tn5B50-378 | 74 ± 7 | 373 ± 60 |
| ::Tn5B50-380 | 18 ± 8 | 96 ± 9 |

*Values represent the mean and standard error of multiple assays and were normalized such that the invasiveness, of aerobically grown SL1344 equals one. The actual percentage of the aerobic SL1344 inoculum that entered HEp-2 cells in one hour was 0.11 0.018%.

In order to determine whether the insertions affect the same or different genes, the mutations were mapped relative to one another by transduction. This was possible since Tn5 encodes kanamycin-resistance whereas Tn/10 and Tn5B50 encode tetracycline resistance. For example, Tn10-181 was found to be >95% linked to Tn5-300 since transduction of Tn/10-181 into a strain carrying Tn5-300 resulted in frequent loss of kanamycin-resistance. In this way, the sixteen mutations were found to define three linkage groups; eleven were in group A, three were in group B and two were in group C.

Groups A and B each contained Tn10, Tn5 and Tn5B50 mutations. In contrast, group C contained only Tn5B50 mutations, specifically, Tn5B50-378 and Tn5B50-380.

The transposons Tn10 and Tn5 insert into genes and disrupt their function. However, Tn5B50, which contains the constitutive neo promoter at one end, cannot only cause genetic disruption but can also result in constitutive expression of an intact gene(s) from the neo promoter. The isolation of both Tn10 and Tn5 mutations in groups A and B indicate that disruption of genes increase the ability of these mutants to enter HEp-2 cells. In contrast, the identification of the C mutants solely from Tn5 B50 mutagenesis indicates that these mutants are better able to enter HEp-2 cells due to the expression of a gene(s) from the neo promoter at the end of the transposon.

Identification of che mutants

In order to identify the genetic lesion in group A mutants, S. typhimurium DNA flanking the Tn10-181 group A insertion was cloned, sequenced and examined for homology to previously identified genes. Tn10-181 was found to be inserted in one of the chemotaxis (che) operons and results in a non-chemotactic phenotype. The che genes allow Salmonella to bias their movement toward attractants or away from repellents by modulating the frequency of smooth swimming versus tumbling behavior (Neidhardt, F. C., Ingraham, J. L., Low, K. B., Magasanik, B., Schaechter, M. and Umbarger, H. E. (1987) in Escherichia coli and Salmonella typhimurium: cellular and molecular biology (American Society for Microbiology, Washington, DC)). Microscopic and swarm plate analysis of the eleven group A mutants confirmed that all are non-chemotactic, specifically due to their inability to tumble (results not shown).

Identification of rho Mutants

In order to identify what genetic sequence was disrupted in the group B mutants, S. typhimurium DNA flanking the Tn5-317 group B insertion was cloned, sequenced and examined for homology to previously identified genes. By inference from what is known in E. coli, Tn5-317 was found to be inserted between the −10 and −35 regions of the promoter for the S. typhimurium rho gene. While the Tn5-317 insertion may affect the end of the trx transcript which, in E. coli, terminates in the same region, the position of the insertion more likely affects the expression of rho (Matsumoto, Y., Shigesada, K., Hirano, M. and Imai, M. (1986) J. Bacteriol. 166:945–958). In order to examine whether defects in rho expression result in hyper-invasiveness, isogenic $rho^{ts}$-111 and $rho^+$ derivatives of SL1344 were constructed and tested for invasiveness. The $rho^{ts}$-111 mutation was found to increase bacterial invasion to an even greater extent than the group B transposon mutations (data not shown).

Characterization of the Third Hyper-Invasive Locus (hil)

Tn5B50-378 and Tn5B50-380 were found to define the C linkage group of hyper-invasive mutations. Initially, two independent Tn5 insertions, Tn5-428 and Tn5-429, were isolated by virtue of their linkage to Tn5B50-380. Transduction of the Tn5 mutations into strains containing the Tn5B50 mutations demonstrated that the hyperinvasive mutations were linked since, the two Tn5 mutations were found to be closely linked to both Tn5B50 mutations.

Defined Mud-P22 strains were utilized to determine where the Tn5B50 mutations lay in the S. typhimurium genome. Fragments of S. typhimurium DNA flanking the Tn5-428 and the Tn5B50-380 mutations were used as probes to test for hybridization with phage particle DNA from 70 Mud-P22 strains. The results showed that Tn5-428 and Tn5B50-380 lie between proU at minute 57.5 and cysHIJ at minute 60 on the S. typhimurium chromosome, since in each case, the flanking DNA hybridized to phage particle DNA from the proU1884::Mud-P, cysH1J1574::MudP and purG2149::MudP strains. Subsequent P22-mediated transductional analysis revealed that Tn5-429 is weakly linked (<0.2%) to both srl and mutS. Only 3 of 3569 and 3 of 1833 transductants lost Tn10 mutations in srl and mutS, respectively, as a result of transduction with Tn5-429. Presumably, the gene order is srl -Tn5—mutS—cys.

Figure 1B:
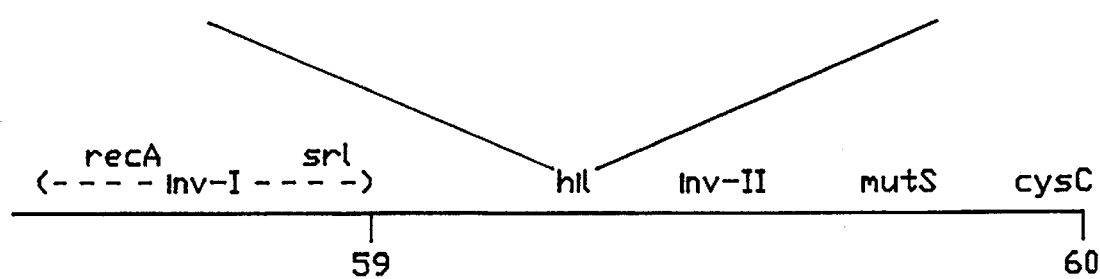
FIG. 1B depicts the genetic map of genes in the 59–60 minute region of the *S. typhimurinm* chromosome. The inv-1 locus consists of four genes interspersed with recA and srl. The orientation of the hil restriction map with respect of the other genes is not known.

The relative positions and orientations of the Tn5B50 mutations in the chromosome were deduced by restriction analysis of chromosomal and cloned DNA from SL1344 and the transposon mutants (FIG. 1A). The results show that the neo promoters of both Tn5B50 mutations are oriented in the same direction and that Tn5B50-378, the strongest hyper-invasive mutation, lies 6.4 kb downstream of Tn5B50-380.

In addition, the site of Tn5-429 insertion was found to lie 2 kb upstream of that of Tn5B50-380 (not shown). We have named this locus hil for hyper-invasion locus.

Characterization of a hil Deletion Mutant

The phenotypic and molecular analysis of the group C hyper-invasive mutations suggests that there is a gene(s) downstream of Tn5B50-378 that acts positively on expression of *S. typhimurium* invasiveness. If this is the case, deletion or disruption of the hil locus might result in loss of invasiveness. Fortuitously, 10 kb of chromosomal DNA downstream of the Tn5B 50-380 mutation was found to be deleted in the Tn5-428 mutant strain (FIG. 1A). Tn5-428 was identified as promoting loss of the tetracycline-resistance phenotype of the Tn5B 50 - 380 mutation by transduction. However, analysis of chromosomal and cloned DNA from the Tn5-428 mutant suggests that the initial recombination of Tn5-428 into the chromosome did not remove the Tn5B50 mutation, instead, tetracycline-resistance apparently was lost by subsequent homologous recombination and deletion between 1550 elements of Tn5B 50 and Tn5.

Analysis of the effect of the hil deletion mutation on bacterial entry into HEp-2 cells showed that this region is essential for expression of *S. typhimurium* invasiveness. Even when grown under low oxygen conditions, the hil deletion mutant was 1000-fold less able to enter HEp-2 cells than the comparably grown parental strain (results not shown).

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A mutant *Salmonella typhimurium* microorganism wherein a hil gene of the hyper-invasive locus located on the 20 kb fragment shown in FIG. 1A has been modified to alter the invasive phenotype of said mutant *Salmonella*.

2. The mutant *Salmonella typhimurium* of claim 1 wherein said hyper-invasive locus has been modified by the substitution, insertion or deletion of one or more nucleotides.

3. The mutant *Salmonella typhimurium* of claim 1 wherein said hyper-invasive locus has been modified by the deletion of more than one nucleotides from said hil gene.

4. The mutant *Salmonella typhimurium* of claim 1 wherein said hyper-invasive locus has been modified to alter expression from said locus.

5. The mutant *Salmonella typhimurium* of claim 1 wherein said altered invasiveness phenotype comprises an increase in invasiveness.

6. The mutant *Salmonella typhimurium* of claim 1 wherein said altered invasiveness phenotype comprises a decrease in invasiveness.

7. A composition comprising the mutant *Salmonella typhimurium* of claim 1 in an mount sufficient to provide an immune response from a mammalian host and a physiologically acceptable carrier.

8. The composition of claim 7 wherein said mutant *Salmonella typhimurium* further comprises exogeneous DNA encoding an immunogen.

9. The composition of claim 8 wherein said immunogen is selected from the group consisting of surface membrane proteins, capsid proteins or envelope proteins from a pathogen.

* * * * *